US008124393B2

(12) United States Patent
Potter et al.

(10) Patent No.: US 8,124,393 B2
(45) Date of Patent: Feb. 28, 2012

(54) COMPOSITIONS AND METHODS FOR INDUCING OR INHIBITING ACTIVITIES OF SELECTED HUMAN CELLS

(75) Inventors: Philip M. Potter, Memphis, TN (US); Monika Weirdl, Memphis, TN (US); Matthew R. Redinbo, Chapel Hill, NC (US)

(73) Assignees: St. Jude Children's Research Hospital, Memphis, TN (US); The University of North Carolina, Chapel Hill, NC (US)

( * ) Notice: Subject to any disclaimer, the term of this patent is extended or adjusted under 35 U.S.C. 154(b) by 9 days.

(21) Appl. No.: 13/020,871

(22) Filed: Feb. 4, 2011

(65) Prior Publication Data

US 2011/0165141 A1 Jul. 7, 2011

Related U.S. Application Data

(62) Division of application No. 12/306,031, filed as application No. PCT/US2007/071640 on Jun. 20, 2007, now Pat. No. 7,906,637.

(60) Provisional application No. 60/805,643, filed on Jun. 23, 2006.

(51) Int. Cl.
*C12N 9/18* (2006.01)
*A61K 38/43* (2006.01)
*A61K 38/00* (2006.01)

(52) U.S. Cl. .......................... 435/197; 424/94.1; 514/1.1

(58) Field of Classification Search ........................ None
See application file for complete search history.

(56) References Cited

U.S. PATENT DOCUMENTS

2003/0096773 A1 5/2003 Crooke et al. .................. 514/44

OTHER PUBLICATIONS

NCBI Accession No. AF036930 [gi:3219694] with Revision History, Jun. 15, 1998-Jun. 20, 1998.
NCBI Accession No. M73499 [gi:179927] with Revision History, Oct. 31, 1991-Apr. 27, 1993.
Bencharit et al., "Crystal structure of human carboxylesterase 1 complexed with the Alzheimer's drug Tacrine:from binding promiscuity to selective inhibition", Chemistry & Biology 2003 10:341-349.
Bencharit et al., "Structural insights into CPT-11 activation by mammalian carboxylesterases", Nature Structural Biology 2002 9(5):337-342.
Danks et al., "Comparison of activation of CPT-11 by rabbit and human carboxylesterases for use in enzyme/prodrug therapy", Clinical Cancer Research 1999 5:917-924.
Meck et al., "A virus-directed enzyme prodrug therapy approach to purging neuroblastoma cells from hematopoietic cells using adenovirus encoding rabbit carbosylesterase and CPT-11", Cancer Research 2001 61:5083-5089.
Potter et al., "Isolation and partial characterization of a cDNA encoding a rabbit liver carboxylesterase that activates the prodrug irinotecan (CPT-11)", Cancer Research 1998 58:2646-2651.
Humerickhouse et al., "Characterization of CPT-11 hydrolysis by human liver carboxylesterase isoforms hCE-1 and hCE-2", Cancer Research 2000 60:1189-1192.
Khanna et al., "Proficient metabolism of irinotecan by a human intestinal carboxylesterase", Cancer Research 2000 60:4725-4728.
Redinbo et al., "Human carboxylesterase 1:from drug metabolism to drug discovery", Biochemical Society Transactions 2003 31(3):620-624.
Rooseboom et al., "Enzyme-catalyzed activation of anticancer prodrugs", Pharmacological Reviews 2004 56(1):53-102.
Wadkins et al., "Structural constraints affect the metabolism of 7-ethyl-10-[4-(1-piperidino)-1-piperidino]carbonyloxycamptothe cin (CPT-11) by carboxylesterases", Molecular Pharmacology 2001 60:355-362.
Wagner et al., "Efficacy and toxicity of a virus-directed enzyme prodrug therapy purging method:preclinical assessment and application to bone marrow samples from neuroblastoma patients", Cancer Research 2002 62:5001-5007.
Wierdl et al., "Sensitization of human tumor cells to CPT-11 via adenoviral-mediated delivery of a rabbit liver carboxylesterase", Cancer Research 2001 61:5078-5082.
Broomfield and Kirby, Journal of Applied Toxicology, 2001, 21: S53-S46.

*Primary Examiner* — Suzanne M Noakes
*Assistant Examiner* — Jae W Lee
(74) *Attorney, Agent, or Firm* — Licata & Tyrrell P.C.

(57) ABSTRACT

Polynucleotides encoding a mutant human carboxylesterase enzyme and polypeptides encoded by the polynucleotides which are capable of metabolizing a prodrug and inactive metabolites thereof to active drug are provided. Compositions and methods for sensitizing cells to a prodrug agent, inhibiting cell growth, treating drug addiction, and facilitating the metabolism of an organophosphate with this enzyme are also provided. In addition, a screening assay for identification of drugs activated by this enzyme is described.

5 Claims, 5 Drawing Sheets

|  |  | SEQ ID NO: |
|---|---|---|
|  | 356               371 |  |
| rCE | GWIIPMQMLGYPLSEG | 6 |
|  | ||:|||  :: |||||| |  |
| hCE1 | GWLIPM-LMSYPLSEG | 7 |
|  |  |  |
| hCE1mut2 | GWLIPM-MLSYPLSEG | 8 |
| hCE1mut3 | GWLIPM-MLSYPLSEG | 8 |
| hCE1mut4 | GWLIPM-MLSYPLSEG | 8 |
| hCE1mut5 | GWIIPM-MLGYPLSEG | 9 |
| hCE1mut6 | GWIIPMQMLGYPLSEG | 10 |

|  |  | SEQ ID NO: |
|---|---|---|
|  | 448               465 |  |
| rCE | YRYRPSFSSDMRPKTVIG | 11 |
|  | :.|||||||||:|||||| |  |
| hCE1 | FQYRPSFSSDMKPKTVIG | 12 |
|  |  |  |
| hCE1mut2 | FQYRPSFSSDMKPKTVIG | 12 |
| hCE1mut3 | FQYRPSFSSDMRPKTVIG | 13 |
| hCE1mut4 | YRYRPSFSSDMRPKTVIG | 14 |
| hCE1mut5 | YRYRPSFSSDMRPKTVIG | 14 |
| hCE1mut6 | YRYRPSFSSDMRPKTVIG | 14 |

FIG. 1A

```
hCE1  MWLRAFILATLSASAAWGHPSSPPVVDTVHGKVLGKFVSLEGFAQPVAIFLGIPFAKPPL  60
 rCE  MWLCALALASLAACTAWGHPSAPPVVDTVHGKVLGKFVSLEGFAQPVAVFLGVPFAKPPL  60
      *** *: **:*:*..:***.:*****************:*.******* hCE1  GPLRFTPPQPAEPWSFVKNATSYPPMCTQDPKAGQLLSELFTNRKENIPLKLSEDCLYLN 120
 rCE  GSLRFAPPQPAESWSHVKNTTSYPPMCSQDAVSGHMLSELFTNRKENIPLKFSEDCLYLN 120
      *.*.**..*.***.. :*:;************:***** hCE1  IYTPADLTKKNRLPVMVWIHGGGLMVGAASTYDGLALAAHENVVVVTIQYRLGIWGFFST 180
 rCE  IYTPADLTKRGRLPVMVWIHGGGLMVGGASTYDGLALSAHENVVVVTIQYRLGIWGFFST 180
      *******:..:**********.****:******************** hCE1  GDEHSRGNWGHLDQVAALRWVQDNIASFGGNPGSVTIFGESAGGESVSVLVLSPLAKNLF 240
 rCE  GDEHSRGNWGHLDQVAALRWVQDNIANFGGDPGSVTIFGESAGGQSVSILLLSPLTKNLF 240
      *************************.***.*************.***:*:****:****

hCE1  HRAISESGVALTSVLVKKGDVKPLAEQIAITAGCKTTTSAVMVHCLRQKTEEELLETTLK 300
 rCE  HRAISESGVALLSSLFRKN-TKSLAEKIAIEAGCKTTTSAVMVHCLRQKTEEELMEVTLK 299
      *********** * *.:*. .*.*:*.*********************:*.*** hCE1  MKFLSLDLQGDPRESQPLLGTVIDGMLLLKTPEELQAERNFHTVPYMVGINKQEFGWLIP 360
 rCE  MKFMALDLVGDPKENTAFLTTVIDGVLLPKAPAEILAEKKYNMLPYMVGINQQEFGWIIP 359
      ***::***.***:*. ..:* *****:** *:* *: **:::. :*******:*****:**

hCE1  M-LMSYPLSEGQLDQKTAMSLLWKSYPLVCIAKELIPEATEKYLGGTDDTVKKKDLFLDL 419
 rCE  MQMLGYPLSEGKLDQKTATELLWKSYPIVNVSKELTPVATEKYLGGTDDPVKKKDLFLDM 419
      * :: ******.******..******:*  .***.*.***********.*********:

hCE1  IADVMFGVPSVIVARNHRDAGAPTYMYEFQYRPSFSSDMKPKTVIGDHGDELFSVFGAPF 479
 rCE  LADLLFGVPSVNVARHHRDAGAPTYMYEYRYRPSFSSDMRPKTVIGDHGDEIFSVLGAPF 479
      :::** *:*********:: ****:******:*:**** hCE1  LKEGASEEEIRLSKMVMKFWANFARNGNPNGEGLPHWPEYNQKEGYLQIGANTQAAQKLK 539
 rCE  LKEGATEEEIKLSKMVMKYWANFARNGNPNGEGLPQWPAYDKKEGYLQIGATTQAAQKLK 539
      ***::**:************:.*::******:***** hCE1  DKEVAFWTNLFAKKAVEKPPQTEHIEL 566    (SEQ ID NO:1)
 rCE  DKEVAFWTELWAKEAAR-PRETEHIEL 565    (SEQ ID NO:2)
      ********:*:**:*.. * :******
```

FIG. 1B

COMPOSITIONS AND METHODS FOR INDUCING OR INHIBITING ACTIVITIES OF SELECTED HUMAN CELLS

This application is a divisional of U.S. Ser. No. 12/306,031 filed Jan. 28, 2009 now U.S. Pat. No. 7,906,637, which is the U.S. National Phase of PCT/US2007/071640 filed Jun. 20, 2007 which claims benefit of U.S. Provisional Ser. No. 60/805,643, filed Jun. 23, 2006, the content of which is incorporated herein by reference in its entirety.

This invention was made with government support under grant numbers CA76202, CA79763, CA98468, CA108775, DA18116 awarded by National Institutes of Health and grant number P30 CA 21765 awarded by Cancer Center Core. The government has certain rights in the invention.

BACKGROUND OF THE INVENTION

1. Field of the Invention

This invention relates to novel polynucleotides which encode a mutant human carboxylesterase enzyme, polypeptides encoded by these polynucleotides and vectors and host cells comprising these vectors which express the enzyme. This enzyme is capable of metabolizing chemotherapeutic prodrugs and inactive metabolites into active drug. The instant invention thus relates to compositions comprising these polynucleotides and methods for sensitizing selected cells to a prodrug by transfecting the cells with a polynucleotide placed under the control of a disease-specific responsive promoter. Sensitized cells can then be contacted with a prodrug to alter the activity of the cell in some manner, such as inhibition of tumor cell growth. Alternative methods contemplated by the invention would apply to treatment of drug addiction and resistance to chemical weapons. The invention further includes novel drug screening assays for identifying new prodrugs that are activated by this enzyme.

2. Background of the Invention

Development of effective human anti-cancer drugs has often been hindered by the inability of tested agents to selectively target tumor cells over non-tumor cells. This lack of selectivity of many anti-cancer drugs often leads to unwanted and often serious side effects in patients that can limit the dose of the drug administered. A goal of all human drug therapies, regardless of the disease or condition being treated, is to be able to administer the lowest dose of a drug that produces the desired clinical effect. Therefore, strategies for more efficient drug delivery are continuously sought.

In the case of certain anti-cancer drugs, one strategy has been development of prodrug forms of active compounds that can increase the bioavailability of the drug and increase its ability to effectively kill tumor cells. One example of this prodrug strategy has been the development of carboxylesterase (CE) pro-drugs (Roosebaum, et al. 2004. *Pharmacol. Rev.* 56:53-102).

CEs are ubiquitous serine esterase enzymes that catalyze conversion of carboxylic esters to an alcohol and a carboxylic acid as well as hydrolyzing amides, thioesters, phosphoric acid esters and acid anhydrides. In some cases, CE enzyme activity is responsible for the detoxification of xenobiotics. CEs are present in high levels in both normal and tumor tissue, especially in liver, kidney, testis, lung and plasma. In addition to their known ability to detoxify certain chemicals, recent research has focused on the ability of these enzymes to be used in design of prodrug forms of certain cytostatic drugs (Roosebaum, et al. 2004. *Pharmacol. Rev.* 56:53-102). Examples of the application of CE activity to prodrug development are CPT-11, paclitaxel-2-ethylcarbonate, and capecitabine. In all three of these cases, CE activity leads to production of an active cytostatic drug, SN-38, paclitaxel, and 5'-DUFR, respectively. In addition, a particular human CE known as hCE1 has been shown to catalyze the hydrolysis of certain drugs of abuse, specifically heroin and cocaine, and to catalyze the transesterification of cocaine in the presence of ethanol to its toxic metabolite, cocaethylene (Redinbo, et al. 2003. *Biochem. Soc. Trans.* 31:620-624). hCE1 is also being developed by the United States military as a prophylactic agent for treating potential exposures to chemical weapons such as the organophosphates Sarin, Soman, Tabun, and VX gas (Redinbo, et al. 2003. *Biochem. Soc. Trans.* 31:620-624).

CPT-11 (irinotecan, 7-ethyl-10-[4-(1-piperidino)-1-piperidino]carbonyloxycamptothecin) is a prodrug that has been investigated for the treatment of cancer, and is converted to the active drug known as SN-38 (7-ethyl-10-hydroxy-camptothecin) (Tsuji, et al. 1991. *J. Pharmacobiol. Dynamics* 14:341-349; Satoh, et al. 1994. *Biol. Pharm. Bull.* 17:662-664). SN-38 is a potent inhibitor of topoisomerase I (Tanizawa, et al. 1994. *J. Natl. Cancer Inst.* 86:836-842; Kawato, et al. 1991. *Cancer Res.* 51:4187-4194), an enzyme whose inhibition in cells results in DNA damage and induction of apoptosis (Hsiang, et al. 1989. *Cancer Res.* 49:5077-5082). In addition to metabolism to SN-38, in humans CPT-11 is also metabolized to a compound known as APC (Haaz, et al. 1998. *Cancer Res.* 58:468-472). APC has little, if any, anti-tumor activity and is not converted to an active metabolite in humans (Rivory, et al. 1996. *Cancer Res.* 56:3689-3694). CPT-11 has demonstrated remarkable anti-tumor activity in pre-clinical models and Phase I/II clinical trials (Furman, et al. 1999. *J. Clin. Oncol.* 17:1815-1824; Houghton, et al. 1996. *Clin. Cancer Res.* 2:107-118; Houghton, et al. 1995. *Cancer Hcemother. Pharmacol.* 36:393-403), and as such is being tested against a variety of human malignancies. However, myelosuppression and secretory diarrhea limit the amount of drug that can be administered to patients. Accordingly, before this promising anti-cancer agent can be used successfully, these dose-limiting toxicities must be overcome. CPT-11 is currently approved for use in human colon cancer.

The active anti-tumor agent of CPT-11, SN-38, can be detected in the plasma of animals and humans minutes after the administration of CPT-11 (Stewart, et al. 1997. *Cancer Chemother. Pharmacol.* 40:259-265; Kaneda, et al. 1990. *Cancer Res.* 50:1715-1720; Rowinsky, et al. 1994. *Cancer Res.* 54:427-436), suggesting that a CE enzyme present in either serum or tissues can convert the camptothecin analog to its active metabolite. When CPT-11 is administered to humans, typically less than 5% of the drug is converted to SN-38, which is in contrast to mice where greater than 50% of the drug is hydrolyzed to SN-38 within the first hour of dosing (Morton, et al. 2005. *Cancer Chemother. Pharmacol.* 56:629-636). This may be due to either the different levels of CEs expressed in these species, or the proficiency of drug hydrolysis of the different CEs.

Since the activation of CPT-11 in humans is relatively inefficient, CE enzyme prodrug therapy approaches have been examined. For example, an enzyme/prodrug therapy approach using a rabbit liver CE (rCE) which is much more efficient at drug activation has been developed (Danks, et al. 1999. *Cancer Res.* 5:917-924; Meck, et al. 2001. *Cancer Res.* 61:5083-5089; Potter, et al. 1998. *Cancer Res.* 52:2646-2651; Wagner, et al. 2002. *Cancer Res.* 62:5001-5007; Wierdl, et al. 2001. *Cancer Res.* 61:5078-5082). Using the rCE in therapy, increased sensitivity to CPT-11 was accomplished in human tumor cells grown in culture and in xenografts in immune-deprived mice. It has been suggested, however, that the application of the rCE to human therapy may be limited due to the potential immunogenicity of the lagomorph protein. Human CE enzymes have been examined, but, in vitro studies suggest that human intestinal CE (hiCE) is not as efficient at drug activation when compared to rCE (Humerickhouse, et al. 2000. *Cancer Res.* 60:1189-1192; Khanna, et al. 2000. *Cancer Res.* 60:4725-4728). Additionally, while sensitization of cells to CPT-11 expressing hiCE has been reported (e.g., Khanna, et al. 2000. *Cancer Res.* 60:4725-4728), studies indicate that the levels and duration of hiCE expressed are much lower than can be achieved with rCE.

The development of new effective treatment strategies for cancer is dependent upon the availability of specific drug screening assays. Specific drug screening assays can involve isolated target tissue models, i.e., isolated heart, ileum, vasculature, or liver from animals such as rabbits, rats, and guinea pigs, wherein the target tissue is removed from the animal and a selected activity of that target tissue is measured both before and after exposure to the candidate drug. An example of a selected activity measured in drug screening assays to identify new cancer agents is the activity of enzymes such as topoisomerase I or II, which are known to modulate cell death. Such assays can also be used to screen for potential prodrugs which are converted to the active metabolite in selected tissues or to identify selected tissues capable of converting prodrug to its active metabolite.

However, any molecular event that is shown to be modified by a novel class of compounds can be developed as a screening assay for selection of the most promising compounds for therapeutic development. In fact, the idea of modulating cells at the genomic level has been applied to the treatment of diseases such as cancer. Gene therapy for treatment of cancer has been the focus of multiple clinical trials approved by the National Institutes of Health Recombinant DNA Advisory Committee, many of which have demonstrated successful clinical application (Hanania, et al. 1995. *Am. Jour. Med.* 99:537-552; Johnson, et al. 1995. *J. Am. Acad. Derm.* 32(5): 689-707; Barnes, et al. 1997. *Obstetrics and Gynecology* 89:145-155; Davis, et al. 1996. *Current Opinion in Oncology* 8:499-508; Roth and Cristiano 1997. *J. Natl. Canc. Inst.* 89(1):21-39). To specifically target malignant cells and spare normal tissue, cancer gene therapies must combine selective gene delivery with specific gene expression, specific gene product activity, and, possibly, specific drug activation. Significant progress has been made in recent years using both viral (retrovirus, adenovirus, adeno-associated virus) and nonviral (liposomes, gene gun, injection) methods to efficiently deliver DNA to tumor sites. Genes can be transfected into cells by physical means such as scrape loading or ballistic penetration, by chemical means such as coprecipitation of DNA with calcium phosphate or liposomal encapsulation; or by electro-physiological means such as electroporation. The most widely used methods, however, involve transduction of genes by means of recombinant viruses, taking advantage of the relative efficiency of viral infection processes. Current methods of gene therapy involve infection of organisms with replication-deficient recombinant viruses containing the desired gene. The replication-deficient viruses most commonly used include retroviruses, adenoviruses, adeno-associated viruses, lentiviruses and herpes viruses. The efficacy of viral-mediated gene transfer can approach 100%, enabling the potential use of these viruses for the transduction of cells in vivo.

Adenovirus vector systems in particular have several advantages. These include the fact that non-dividing cells can be transduced; transduced DNA does not integrate into host cell DNA, thereby negating insertional mutagenesis; the design of adenoviral vectors allows up to 7 kb of foreign DNA to be incorporated into the viral genome; very high viral titers can be achieved and stored without loss of infectivity; and appropriate plasmids and packaging cell lines are available for the rapid generation of infectious, replication-deficient virus (Yang 1992. *Crit. Rev. Biotechnol.* 12:335-356). The effectiveness of adenoviral-mediated delivery of genes into mammalian cells in culture and in animals has been demonstrated.

To increase the specificity and safety of gene therapy for treatment of cancer, expression of the therapeutic gene within the target tissue must also be tightly controlled. For tumor treatment, targeted gene expression has been analyzed using tissue-specific promoters such as breast, prostate and melanoma specific promoters and tumor-specific responsive promoters such as carcinoembryonic antigen, HER-2/neu, Myc-Max response elements, DF3/MUC (Dachs, et al. 1997. *Oncol. Res.* 9:313-25). For example, the utility of herpes simplex virus thymidine kinase (HSV-TK) gene ligated with four repeats of the Myc-Max response element, CACGTG, as a gene therapy agent for treatment of lung cancer with ganciclovir was examined in c-, L- or N-myc-overexpressing small cell lung cancer (SCLC) cell lines (Kumagai, et al. 1996. *Cancer Res.* 56(2):354-358). Transduction of the HSV-TK gene ligated to this CACGTG core rendered individual clones of all three SCLC lines more sensitive to ganciclovir than parental cells in vitro, thus suggesting that a CACGTG-driven HSV-TK gene may be useful for the treatment of SCLC overexpressing any type of myc family oncogene. Additional experiments with c-myc have focused on the use of the ornithine decarboxylase (ODC) promoter gene. Within the first intron of the ODC gene are two CACGTG "E boxes" that provide binding sites for the c-myc protein when bound to its partner protein known as max. Mutation of the E box sequence results in the inability of c-myc to transactivate the ODC promoter. Previous reports indicate that reporter constructs containing the ODC promoter fused upstream of the chloramphenicol acetyltransferase gene immediately adjacent to the second exon were activated in cells that overexpress c-myc (Bello-Fernandez, et al. 1993. *Proc. Natl. Acad. Sci. USA* 90:7804-7808). In contrast, transient transfection of promoter constructs in which the E boxes were mutated (CACGTG to CACGTG) demonstrate significantly lower reporter gene activity. These data suggest that it is possible to activate transcription of specific genes under control of the c-myc responsive ODC promoter. In the case of N-myc, N-myc protein is a basic helix-loop-helix (BHLH) protein that can dimerize with proteins of the same class. N-myc dimerizes with the BHLH protein max to form a complex that binds to the CACGTG motif present in gene promoters, such as ODC, resulting in transactivation and expression of specific genes containing this sequence (Lutz, et al. 1996. *Oncogene* 13:803-812). Studies in a neuroblastoma cell line and tumors have shown that binding of N-myc to its consensus DNA binding sequence correlates with N-myc expression, data that indicate that the level of N-myc in neuroblastoma cells is a determining factor in expression of proteins under control of promoters containing the CACGTG sequence (Raschella, et al. 1994. *Cancer Res.* 54:2251-2255). Inhibition of expression of the c-myc gene via antisense oligonucleotides as a means for inhibiting tumor growth has also been disclosed (Kawasaki, et al. 1996. *Artif. Organs* 20(8):836-48).

In the present invention, a mutant human CE has been developed that can activate CPT-11 as efficiently as CE from rabbit liver (rCE). Polynucleotides encoding this mutated human carboxylesterase enzyme or active fragments thereof and polypeptides encoded thereby which are capable of metabolizing the chemotherapeutic prodrug CPT-11 to active drug SN-38 are disclosed. This mutant human carboxylesterase enzyme also has potential applications to treatments involving other potential substrates such as certain drugs of abuse (e.g., cocaine and heroin) and certain types of chemical weapons (e.g., organophosphates). It has also been found that compositions comprising a polynucleotide of the present invention and a disease-specific responsive promoter can be delivered to selected tumor cells to sensitize the tumor cells to the chemotherapeutic prodrug CPT-11, thereby inhibiting tumor cell growth.

SUMMARY OF THE INVENTION

The present invention relates to polynucleotides encoding a mutant human carboxylesterase capable of metabolizing a chemotherapeutic prodrug and inactive metabolites thereof to active drug. Polypeptides encoded by these polynucleotides are also embraced by the present invention as are vectors containing these polynucleotides and host cells harboring vectors which express a mutant human carboxylesterase.

The present invention is also a composition containing a polynucleotide encoding a mutant human carboxylesterase and a disease-specific responsive promoter.

A method for sensitizing tumor cells to a chemotherapeutic prodrug is also provided. This method involves transfecting selected tumor cells with a composition containing a polynucleotide encoding a mutant human carboxylesterase and a disease-specific responsive promoter of the selected tumor cells.

The present invention is also a method of inhibiting growth of selected tumor cells which includes sensitizing selected tumor cells to a chemotherapeutic prodrug metabolized to active drug by a mutant human carboxylesterase and administering a chemotherapeutic prodrug.

The present invention also relates to a method of purging bone marrow cells of tumor cells. This method involves removing bone marrow cells from a patient and contacting the bone marrow cells with the mutant human carboxylesterase of the present invention and a chemotherapeutic prodrug.

Methods for treating drug addiction and facilitating the metabolism of an organophosphate with the mutant human carboxylesterase of the present invention are also provided as are drug screening assays for identification of compounds activated by a mutant human carboxylesterase.

BRIEF DESCRIPTION OF THE DRAWINGS

FIG. 1 depicts rCE and hCE1 amino acid and nucleic acid sequences. FIG. 1A shows the amino acid sequence alignment of residues 356-371 and 448-465 from rCE and hCE1 that form the missing loops from the former enzyme, and a list of hCE1 mutants that were constructed. Underlined residues indicate amino acids that were substituted by mutagenesis. FIG. 1B shows the alignment of full-length wild-type hCE1 (SEQ ID NO:1) and rCE (SEQ ID NO:2) proteins with loop regions of FIG. 1A indicated.

DETAILED DESCRIPTION OF THE INVENTION

Figure 2:
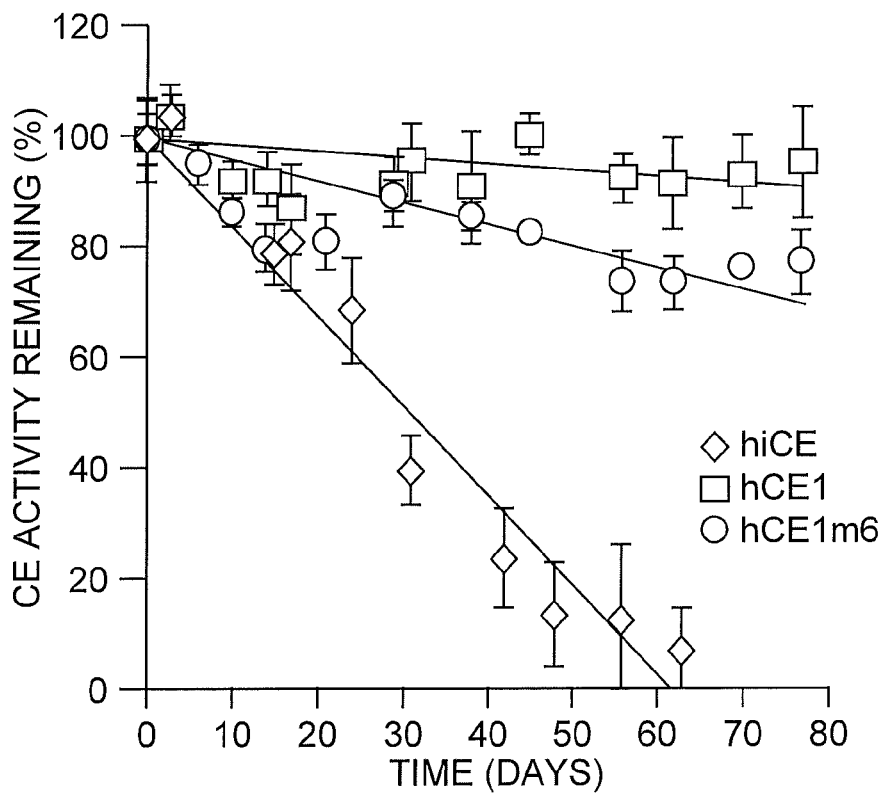
FIG. 2 depicts the in vitro stability of hCE1, hCE1m6 and hiCE. Enzymes were aliquoted in 50 mM Hepes, stored at 20° C. and CE activities were determined at various time intervals, up to 11 weeks. Data are expressed as the amount of active CE remaining as compared to day 0.

CPT-11 is a promising anti-cancer prodrug, that when given to patients, is converted to its active metabolite SN-38 by a human carboxylesterase. However, the wild-type human enzyme is relatively inefficient and less than 5% of the prodrug is metabolized to SN-38 (Rivory, et al. 1997. *Clin. Cancer Res.* 3:1261-1266). In patients, this prodrug is also metabolized to APC (Haaz, et al. 1998. *Cancer Res.* 58:468-472). APC has little, if any, active anti-tumor activity and is not converted to an active metabolite in humans (Rivory, et al. 1996. *Cancer Res.* 56:3689-3694). Accordingly, high concentrations of this prodrug must be administered to achieve effective levels of active drug in vivo. However, myelosuppression and secretory diarrhea limit the amount of prodrug that can be administered to patients.

In the present invention, a method of sensitizing tumor cells to reduce the effective dose of a prodrug required to inhibit tumor cell growth is provided which involves transfecting selected tumor cells with a mutated human CE encoded by a polynucleotide.

In accordance with the present invention, a polynucleotide is provided which encodes a mutated human carboxylesterase capable of metabolizing a chemotherapeutic prodrug and inactive metabolites thereof to active drug. By "polynucleotide" it is meant to include any form of DNA or RNA such as cDNA or genomic DNA or mRNA, respectively, encoding this mutated human enzyme or an active fragment thereof which are obtained by cloning or produced synthetically by well-known chemical techniques. DNA can be double- or single-stranded. Single-stranded DNA can include the coding or sense strand or the non-coding or antisense strand. Thus, the term polynucleotide also includes polynucleotides which hybridize under stringent conditions to the above-described polynucleotides. As used herein, the term "stringent conditions" means at least 60% homology at hybridization conditions of 60° C. at 2×SSC buffer. In a particular embodiment, the polynucleotide is a mutant human cDNA or a homologous sequence or fragment thereof which encodes a polypeptide having similar activity to that of rabbit liver CE enzyme. Due to the degeneracy of the genetic code, polynucleotides of the present invention can also include other nucleic acid sequences encoding this enzyme and derivatives, variants or active fragments thereof. The present invention also relates to variants of this polynucleotide which may be naturally occurring, i.e., allelic variants, or mutants prepared by well-known mutagenesis techniques.

In particular embodiments, the mutant human CE protein of the present invention contains at least the following mutations in reference to a wild-type human CE (set forth herein as SEQ ID NO:1): Leu358Ile, Leu362Met, Met363Leu, Ser364Gly, Phe448Tyr, Gln449Arg, Lys459Arg and insertion of Gln after Met361 (see FIG. 1A). These mutations, when introduced into wild-type human CE produce a polypeptide having similar activity to that of rabbit liver CE enzyme (SEQ ID NO:2). An exemplary mutant human CE polypeptide containing these mutations is set forth herein as SEQ ID NO:3.

Mutation of the wild-type hCE1 protein (SEQ ID NO:1) can be achieved using any conventional mutagenesis approach including site-directed mutagenesis methods well-known in the art with nucleic acids encoding wild-type hCE1 protein as a template. An exemplary wild-type hCE1-encoding nucleic acid molecule is set forth herein as SEQ ID NO:4.

The present invention also provides vectors which harbor polynucleotides of the present invention and host cells which are genetically engineered with vectors of the present invention to produce mutant human CE or active fragments of this enzyme. Generally, any vector suitable to maintain, propagate or express polynucleotides to produce the enzyme in the host cell can be used for expression in this regard. In accordance with this aspect of the invention the vector can be, for example, a plasmid vector, a single- or double-stranded phage vector, or a single- or double-stranded RNA or DNA viral vector. Such vectors include, but are not limited to, chromosomal, episomal and virus-derived vectors, e.g., vectors derived from bacterial plasmids, bacteriophages, yeast episomes, yeast chromosomal elements, and viruses such as baculoviruses, papova viruses, SV40, vaccinia viruses, adenoviruses, fowl pox viruses, pseudorabies viruses and retroviruses, and vectors derived from combinations thereof, such as those derived from plasmid and bacteriophage genetic elements, cosmids and phagemids. Selection of an appropriate promoter to direct mRNA transcription and construction of expression vectors are well-known. In general, however, expression constructs will contain sites for transcription initiation and termination, and, in the transcribed region, a ribosome binding site for translation. The coding portion of the mature transcripts expressed by the constructs will include a translation initiating codon at the beginning and a termination codon appropriately positioned at the end of the polypeptide to be translated. Examples of eukaryotic promoters routinely used in expression vectors include, but are not limited to, the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter. Vectors comprising the polynucleotides can be introduced into host cells using any number of well-known techniques including infection, transduction, transfection, transvection and transformation. The polynucleotides can be introduced into a host alone or with additional polynucleotides encoding, for example, a selectable marker. Host cells for the various expression constructs are well-known, and those of skill can routinely select a host cell for expressing the mutated human CE enzyme in accordance with this aspect of the present invention. Examples of mammalian expression systems useful in the present invention include, but are not limited to, the C127, 3T3, CHO, HeLa, human kidney 293 and BHK cell lines, the COS-7 line of monkey kidney fibroblasts, and neural stem cells. In the case of the use of neural stem cells as a delivery system, U.S. Patent Application Nos. 20050019313 and 20050169897 provide methods for development and application of such cells as a delivery system.

The present invention also relates to compositions containing a polynucleotide of the present invention which have been found to be useful in sensitizing tumor cells to CPT-11 cytotoxicity by combination therapy of the prodrug and a CE enzyme. The present invention thus provides methods for sensitizing tumor cells to a prodrug oncologic agent. In this context, by "sensitizing" it is meant that the effective dose of the prodrug can be reduced when the compositions and methods of the present invention are employed. In a case where the prodrug's therapeutic activity is limited by the occurrence of significant toxicities, or dose-limiting toxicities, sensitization of tumor cells to the prodrug is especially useful.

While rabbit CE (rCE) and human liver CE, (hCE1) are structurally similar, demonstrating 81% amino acid identity (Danks, et al. 1999. *Clin. Cancer Res.* 5:917-924) and only a ~1.0 Å RMSD variation over 455 residues of the α-carbon trace (Danks, et al. 1999. *Clin. Cancer Res.* 5:917-924; Bencharit, et al. 2002. *Nat. Struct. Biol.* 9:337-342; Bencharit, et al. 2003. *Chem. Biol.* 10:341-349), the latter enzyme is very inefficient at CPT-11 activation (100- to 1000-fold lower than rCE. In a comparison of the x-ray crystal structures of rCE and hCE1, two loops in rCE (amino acids 356-371 and 450-465; see FIGS. 1A and 1B) were identified that were apparently missing from the crystal structure of hCE1. These loops formed the entrance to the active site of the protein, and it was assumed that the structures of these domains could not be determined due to enhanced flexibility and thermal motion. It has been reported that the substrate specificity of CEs is in part determined by the constraints enforced by loops that surround the active site entrance (Wadkins, et al. 2001. *Mol. Pharmacol.* 60:355-362). Thus, the more rigid structure of these domains in hCE1 protein may significantly impact the ability of the protein to activate CPT-11. A series of hCE1 mutants was developed that contained multiple amino acid substitutions in these loop regions such that the sequence in these regions was identical to rCE. The five mutants constructed are listed in Table 1 (hCE1mut2 through hCE1mut6). The mutants were inserted into a plasmid, pCIneo, which was obtained from Promega (Madison, Wis.). The cDNAs for the wild-type enzymes are found in Genbank: hCE1, Genbank Accession No. M73499 (SEQ ID NO:4); rCE, Genbank Accession No. AF036930 (SEQ ID NO:5).

TABLE 1

| Name | Mutations |
| --- | --- |
| pCIhCE1mut2 | L362M, M363L |
| pCIhCEmut3 | L362M, M363L, K459R |
| pCIhCEmut4 | L362M, M363L, K459R, F448Y, Q449R |
| pCIhCEmut5 | L362M, M363L, K459R, F448Y, Q449R, L358I, S364G |
| pCIhCEmut6 | L362M, M363L, K459R, F448Y, Q449R, L358I, S364G, Q362 insertion |

Site-directed mutagenesis was used to produce the hCE1 mutants. All mutants were subjected to DNA sequence analysis to confirm the identity of the clones. The mutant cDNAs were expressed from pCIneo in Cos7 cells. In addition to the hCE1 mutants listed in Table 1, a plasmid containing wild-type hCE1 cDNA was constructed (pCIhCE1), and mutant rCE plasmids were also constructed as listed in Table 2.

TABLE 2

| Name | Details |
| --- | --- |
| pCIrCEmut2 | I357L, R459K |
| pCIrCEmut3 | I357L, R459K, M362L |
| pCIrCEmut4 | I357L, R459K, M362L, L363M, Q364S, Y448F, R449Q |
| pCIrCEmut5 | I357L, R459K, M362L, L363M, Q364S, Y448F, R449Q, Q361 deletion |

The CE mutants were then tested to characterize their ability to activate CPT-11. To assess CPT-11 activation by the hCE1 mutant proteins, the cDNAs had been ligated into the expression vector pCIneo and transiently produced the protein in Cos7 cells. Whole cell sonicates were monitored for CE activity. Results were expressed as nmoles o-nitrophenol produced per minute per milligram of total protein. To correct for differences in CE expression within transfected cells, the enzyme activity values were corrected for the level of immunoreactive CE protein as determined using a western bolt analysis. The results of the analysis are shown in Table 3. Following transfection with all hCE1-containing plasmids, all extracts demonstrated CE activity, and all had similar levels of CE protein as determined by western blot analysis using an anti-hCE1 antibody. However, only hCE1mut6 was capable of converting CPT-11 to SN-38.

TABLE 3

| Plasmid | CE Activity (nmol/min/mg) | CPT-11 Converting Activity (pmol/hr/mg CE) |
|---|---|---|
| pCIneo | 5.5 ± 0.1 | Not detected (ND) |
| hCE1 | 119.0 ± 5.0 | ND |
| hCE1mut2 | 267.2 ± 65.2 | ND |
| hCE1mut3 | 158.4.5 ± 20.2 | ND |
| hCE1mut4 | 450.8 ± 45.7 | ND |
| hCE1mut5 | 369.5 ± 26.8 | ND |
| rCE (wild-type) | 332.7 ± 17.2 | 41 |
| hCE1mut6 | 202.8 ± 10.3 | 40.5 |

To directly compare the ability of hCE1m6 and rCE to activate CPT-11, both proteins were expressed in COS-7 cells and the ability of extracts to hydrolyze the drug was assessed. In these studies, the levels of CPT-11 activation were corrected for the amounts of CE protein in the cell extracts by western analysis. This was necessary since it was unclear whether the mutations would influence the ability of the CEs to metabolize o-NPA, which is used as a measure of enzyme activity. As indicated in Table 3, hCE1m6 and rCE were essentially equally efficient at CPT-11 hydrolysis.

Since mutation of the loop domain in hCE1 with residues present in rCE increased the ability of the wild-type hCE1 protein to hydrolyze CPT-11, it was postulated that the converse mutations (i.e., hCE1 residues substituted into rCE) would reduce the ability of rCE to activate CPT-11. This panel of mutant rCE proteins is listed in Table 2. The ability of these mutants to convert CPT-11 to SN-38 was then assessed using the methods described above. The results are listed in Table 4.

TABLE 4

| Plasmid | CE Activity (nmol/min/mg CE) | CPT-11 Converting Activity (pmol/hr/mg CE) |
|---|---|---|
| rCE (wild-type) | 243.1 ± 17.0 | 75.6 |
| rCEmut2 | 333.1 ± 7.0 | 52.5 |
| rCEmut3 | 170.7 ± 11.0 | 47.4 |
| rCEmut4 | 141.4 ± 1.8 | 41.7 |
| rCEmut5 | 219.9 ± 5.8 | 11.5 |
| hCE1 (wild-type) | 329.2 ± 11.6 | Not Detected |

Substitution of the amino acids present within loops of rCE with corresponding residues from hCE1 resulted in a gradual reduction in the ability of the protein to hydrolyze CPT-11. A mutant that contained eight amino acid changes, rCEmut5, was 7-fold less efficient at drug activation than wild-type rCE. Mutants with intermediate numbers of amino acid substitutions demonstrated intermediate abilities to hydrolyze CPT-11. These data demonstrate that there was a gradient of catalytic activity, where the mutant with the smallest number of substitutions demonstrated the lowest reduction in ability to hydrolyze CPT-11.

To directly compare the abilities of the mammalian CEs to hydrolyze CPT-11, a series of biochemical studies were carried out using the purified proteins in vitro. These experiments determined the $K_m$, $V_{max}$, $k_{cat}$ and $k_{cat}/K_m$ values for the different enzymes. As indicated in Table 5, hCE1m6 was ~70-fold more efficient at CPT-11 hydrolysis as compared to the hCE1. In addition, hCE1m6 was almost as effective at CPT-11 hydrolysis as hiCE. It should be noted that both hiCE and hCE1m6 were less efficient at drug activation than rCE, however since hiCE has been effectively used in prior enzyme/prodrug therapy approaches (Oosterhoff, et al. 2005. *Br. J. Cancer* 92:882-887; Oosterhoff, et al. 2002. *Br. J. Cancer* 87:659-664; Oosterhoff, et al. 2005. *Gene Ther.* 12:1011-1018; Oosterhoff, et al. 2003. *Mol. Cancer Ther.* 2:765-771), hCE1m6 is expected to be efficacious in CPT-11 activation in vivo.

TABLE 5

| Enzyme | Km (μM) | Vmax (nmol/min/mg) | $k_{cat}/K_m$ (mM$^{-1}$ min$^{-1}$) | Ratio $k_{cat}/K_m$ as compared to hCE1 |
|---|---|---|---|---|
| hCE1[a] | 82.8 ± 9.6 | 0.36 ± 0.017 | 0.28 | 1 |
| hCE1m6 | 6.25 ± 0.59 | 2.11 ± 0.06 | 19.8 | 71 |
| rCE[a] | 6.20 ± 0.63 | 18 ± 0.9 | 180.0 | 650 |
| hiCE | 3.35 ± 0.34 | 1.49 ± 0.04 | 25.2 | 91 |

[a]Data taken from Wadkins, et al. 2001. Mol. Pharmacol. 60: 355-362 (29).

In previous biochemical experiments, it was noted that in vitro purified hiCE was much less stable than hCE1. Therefore, the loss of CE activity was evaluated in preparations of these proteins, as well as hCE1m6 that had been stored at room temperature. In these studies, purified protein was aliquoted in 50 mM Hepes pH7.4, and enzyme activity was determined over a period of 12 weeks. As indicated in FIG. 2, hiCE was the least stable protein, losing 50% of its activity by ~30 days. In contrast, both hCE1m6 and hCE1 were relatively stable under these conditions with predicted half-lives of 129 and 440 days, respectively.

In in vivo studies, it was observed that expression of hiCE following plasmid-mediated transfection was frequently lower than that seen with rCE or hiCE. Therefore, U373MG cells expressing hiCE, hCE1 or hCE1m6 were developed using the plasmid pIRESneo, and CE expression in the derived lines was monitored over an extended time period. Since expression of the transgene from this expression vector is co-regulated with the neo gene via an IRES sequence, selection with similar concentrations of G418 should result in cell lines that express approximately equal levels of recombinant protein. However, the average levels of CE activity in U373hiCE, U373hCE1 and U373hCE1m6 cells were 287.6±76.6, 1077.1±77.5, and 466.5±52.6 nmoles/min/mg, respectively. Since high level expression of the prodrug-activating protein would be necessary for effective application of enzyme/prodrug therapy, hiCE may not be the best CE for activating CPT-11.

Figure 3:
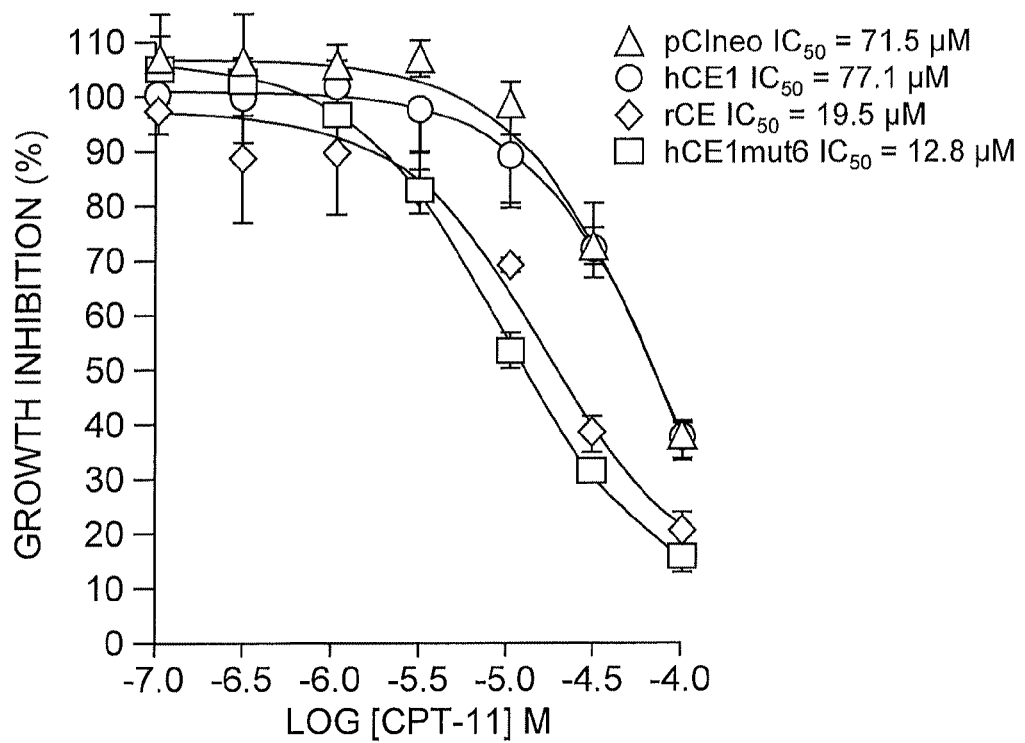
FIG. 3 depicts the growth inhibition curves for COST cells treated with CPT-11.

The sensitivity of mammalian cells to CPT-11 following expression of hCE1mut6 was then determined by constructing cell growth inhibition curves for human tumor cells expression the mutant protein. Cos7 cells transiently transfected with hCE1mut6, as described above, were contacted with increasing concentrations of CPT-11 in order to determine the concentration of drug required to inhibit cell growth by 50% ($IC_{50}$). FIG. 3 shows that cells expressing the hCE1mut6 protein were equally as sensitive to CPT-11 as cells expressing rCE. Both populations of cells had similar $IC_{50}$ values for CPT-11, approximately 12 to 20 micromolar. This value was 5-fold less that the $IC_{50}$ value for cells expressing wild-type hCE1 ($IC_{50}$=77.1 micromolar).

Experiments were also performed in human brain tumor cells (U373MG) where the growth of the cells was examined in cells that expressed the mutant form of the human CE enzyme. As indicated in Table 6, cells expressing hCE1m6, hiCE or rCE were sensitized to CPT-11 due to intracellular conversion of the drug to SN-38. Cells expressing hCE1 were not sensitized, consistent with the lack of CPT-11 hydrolysis observed in the biochemical studies. Furthermore, U373MG cells expressing hCE1m6 were equally as sensitive to CPT-11 as cells expressing rCE, with $IC_{50}$ values ranging from 0.18-0.40 μM. These values were ~18- to 86-fold less than cells expressing wild-type hCE1 ($IC_{50}$ value=15.5 μM). These results indicate that hCE1mut6 can efficiently convert CPT-11 to SN-38 intracellularly and sensitize cells to the drug.

TABLE 6

| Cell line | Adenovirus | Enzyme expressed | CE activity (nmol/min/mg ± SD) | CPT-11 $IC_{50}$ (μM) | Fold decrease in $IC_{50}$* |
|---|---|---|---|---|---|
| U373IRES | — | None | 10.0 ± 0.3 | 24.0 | — |
| U373hCE1 | — | hCE1 | 1016.4 ± 45.5 | 15.5 | — |
| U373hiCE | — | hiCE | 408.2 ± 5.6 | 0.84 | 18 |
| U373rCE | — | rCE | 601.0 ± 20.5 | 0.40 | 39 |
| U373hCE1m6 | — | hCE1m6 | 437.3 ± 37.5 | 0.18 | 86 |
| U373MG | AdVC | None | 10.0 ± 0.5 | 26.8 | — |
|  | AdCMVrCE | rCE | 1076.8 ± 67.3 | 0.3 | 89 |
|  | AdCMVhCE1m6 | hCE1m6 | 5999.8 ± 162.5 | 0.04 | 670 |
| Rh30 | AdVC | None | 4.6 ± 0.3 | 64.3 | — |
|  | AdCMVrCE | rCE | 665.6 ± 52.0 | 3.4 | 29 |
|  | AdCMVhCE1m6 | hCE1m6 | 2757.6 ± 87.5 | 2.0 | 32 |
| SK-N-As | AdVC | None | 6.9 ± 0.3 | 31.7 | — |
|  | AdCMVrCE | rCE | 2150.3 ± 105.9 | 0.6 | 53 |
|  | AdCMVhCE1m6 | hCE1m6 | 6225.0 ± 113.4 | 0.5 | 63 |

*value as compared to U373MGhCE1 or cell line + AdVC.

Figure 4:
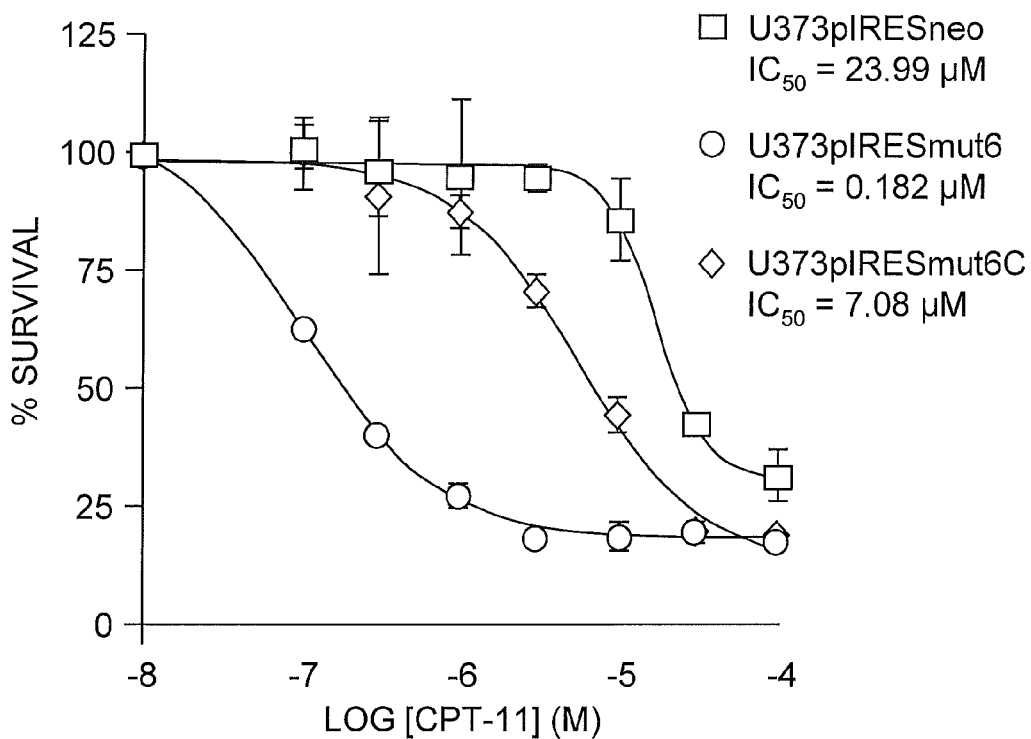
FIG. 4 depicts growth inhibition curves for U373MG cells (brain tumor cell line) expressing either the intracellular (u373IRESmut6) or the secreted form (U373IRESmut6C) of hCE1mut6, which were treated with CPT-11.

Experiments were also performed to determine whether cells expressing a secreted form of hCE1m6 produced media that had CE activity. U373MG cells expressing either the intracellular (u3731RESmut6) or the secreted form (U373IRESmut6C) of hCE1mut6 were treated with CPT-11. There was an approximate 130-fold reduction in the $IC_{50}$ value for CPT-11 in the cells expressing hCE1mut6 (either form). However, cells expressing the secreted form of the protein had an intermediate $IC_{50}$ for CPT-11 (7.08 μM) because the intracellular levels of the CE were lower due to the secretion into the culture media (FIG. 4).

Figure 5:
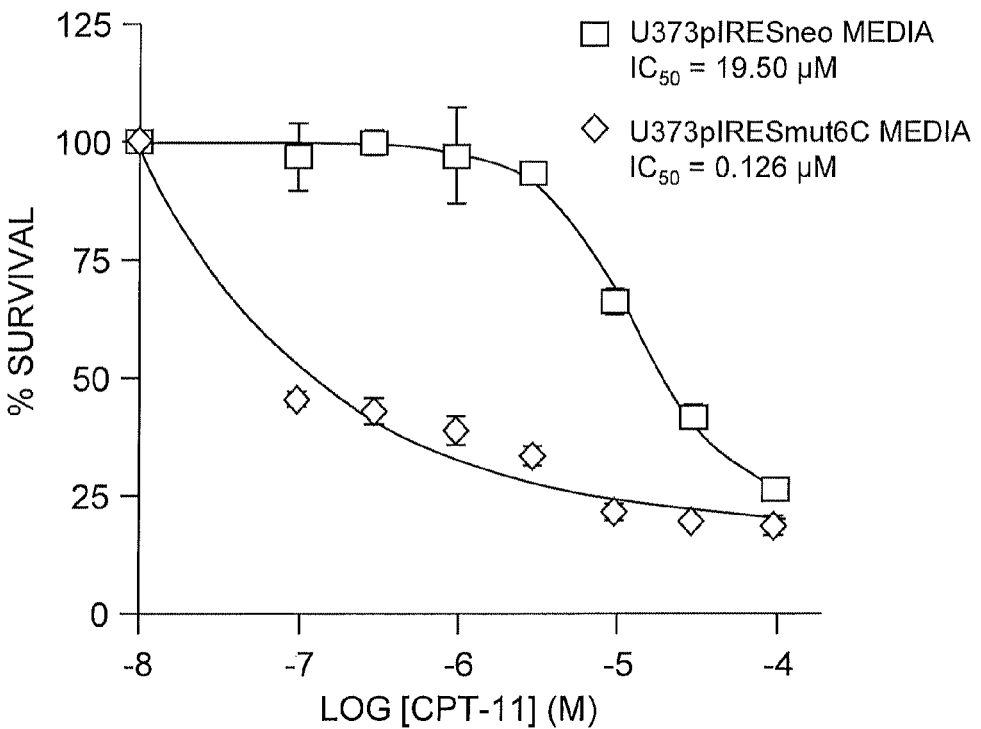
FIG. 5 depicts growth inhibition curves with CPT-11 treatment in untransfected U373MG cells incubated with the media harvested control cells (pIRESneo) or cells expressing the secreted form of hCE1mut6 (pIRESmut6C).

Growth inhibition of untransfected U373MG cells was also examined following incubation with the media harvested control cells (pIRESneo) or cells expressing the secreted form of hCE1mut6 (pIRESmut6C) and CPT-11. Since the enzyme was secreted into the media and able to activate CPT-11, the active metabolite SN-38 was produced, resulting in cytotoxicity to cells that did not express the mutant CEs. This effect was not observed with the control media. The difference in the $IC_{50}$ values was approximately 150-fold (FIG. 5). These results are indicative of a bystander or collateral effect.

Figure 6:
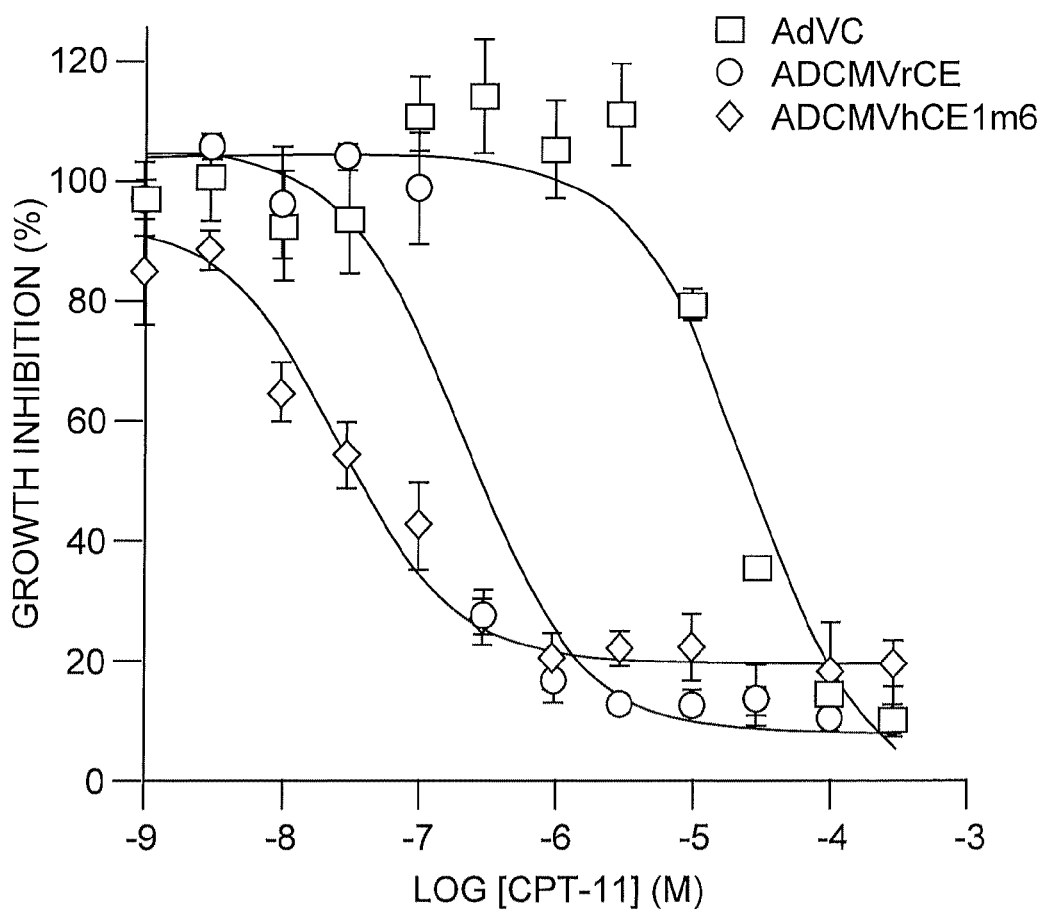
FIG. 6 shows growth inhibition curves for U373MG cells transduced with AdVC, ADCMVrCE, or ADCMVhCE1m6, following treatment with CPT-11. The $IC_{50}$ values for these cells with CPT-11 are 26.8 µM, 0.3 µM and 0.04 µM, respectively.

E1A, E3-deleted replication-deficient adenovirus expressing hCE1m6 were also generated and the ability of this vector to sensitize cells to CPT-11 was determined. As shown in Table 6, in all human tumor cell lines, expression of hCE1m6 significantly decreased the CPT-11 $IC_{50}$ values as compared to vector transduced cells. In SK-N-As and Rh30 cell lines, the CPT-11 sensitivity was comparable to cells transduced with AdCMVrCE (adenovirus containing the rabbit liver CE cDNA), with $IC_{50}$ values of 2 nM and 0.6 nM, respectively. However, the human astrocytoma cell line U373MG, was 7.5-fold more sensitive to CPT-11 after AdCMVhCE1m6 transduction, than after exposure to AdCMVrCE. This resulted in an overall reduction in the $IC_{50}$ for CPT-11 of ~670-fold for U373MG cells (FIG. 6), the greatest sensitization observed using this enzyme/prodrug approach. Overall, these results indicate that AdCMVhCE1m6 can sensitize cells to CPT-11 as effectively as AdCMVrCE, and that the former vector should be suitable for enzyme/prodrug therapy with this drug.

Thus, one embodiment of the present invention embraces transfecting selected tumor cells with the polynucleotide of the present invention, which expresses mutant human CE. The polynucleotide can expressed via a well-known promoter such as the CMV promoter or, more preferably, via a disease-specific responsive promoter which specifically targets the selected tumor cells. Targeted gene expression in tumor cells has been achieved using disease-specific responsive promoters such as carcinoembryonic antigen, HER-2/neu, Myc-Max response elements, and DF3/MUC. Thus, a composition containing the mutant CE disclosed herein and a disease-specific responsive promoter such as these can be used to transfect and sensitize tumor cells containing the disease-specific responsive promoter. Accordingly, the present invention provides a means for exploiting tumor-specific expression associated with a disease-specific responsive promoter to provide for selective therapy of tumors.

Since myc expression is deregulated in a wide variety of human tumors, myc is an attractive target for chemotherapeutics. No known drug specifically interacts with either the c-myc or N-myc protein. However, cells overexpressing a myc oncogene can be targeted with compositions of the present invention containing a polynucleotide of the present invention under the control of a myc specific promoter. Thus, using the present invention the tumor-specific overexpression of c-myc and N-myc can be exploited to produce selective killing with a chemotherapeutic agent.

In vivo efficacy of the CE of the present invention to sensitize tumor cells to CPT-11 is examined in different types of tumor cells as well as in a mouse model to demonstrate that the mutant human CE of the present invention is capable of sensitizing cells to the growth inhibitory effects of CPT-11.

For example, the ability of the mutant human CE, hCE1mut6, to sensitize Rh30 rhabdomyosarcoma human tumor cells grown as xenografts in immune-deprived mice can be examined. This is a well-accepted preclinical model, where expression of the transfected cDNA for hCE1mut6 can first be established. Following establishment of tumors in the animals, treatment with CPT-11 begins. Tumor growth is examined and compared in animals treated with CPT-11 when the tumor cells had been transfected with the mutant human CE versus the growth seen in tumor cells not transfected with this mutant human CE, or those transfected with other CE forms, such as rCE. The in vivo effects of the hCE1mut6 protein can also be examined in a model such as mice with human U373 glioblastoma xenografts, where the xenografts express hCE1mut6. Again, the sensitivity of these tumor cells to CPT-11 can be compared to xenografts transfected with a control plasmid.

The data described herein support the use of the combination of polynucleotide encoding a mutant CE of the present invention and CPT-11 to reduce the amount of CPT-11 needed to produce inhibition of tumor cell growth, or to sensitize the tumor cells to CPT-11. These data can also be used to support the use of the present invention to allow for decreased dosage with CPT-11 in cancer patients, thus reducing the likelihood of dose-limiting toxicity.

The present invention thus also relates to a method for treating cancer with reduced side effects. In one embodiment, a polynucleotide of the present invention is inserted into a viral vector using a gene transfer procedure. Preferred viral vectors include, but are not limited to, retroviral, adenoviral, herpesvirus, vaccinia viral and adeno-associated viral vectors. In this embodiment, it is preferred that the vector further include a disease-specific responsive promoter. The vectors can then be injected into the site of tumor removal along with systemic administration of a prodrug such as CPT-11 to inhibit the recurrence of tumors due to residual tumor cells present after surgical resection of a tumor.

Alternatively, the viral vector can be used to purge bone marrow of contaminating tumor cells during autologous transplant. Bone marrow purging via a viral vector such as adenovirus which expresses a CE of the present invention is performed ex vivo. Efficiency of removal of contaminating tumor cells is determined by PCR assays of purged samples. Data indicate that the method of the present invention is applicable to an animal model for purging bone marrow of neuroblastoma cells such as that described in Example 6. Methods for preparation of the vectors, modes of administration, and appropriate doses of prodrug are well-known to those of skill in the art. Other methods of gene delivery such as chemical and liposome-mediated gene transfer, receptor-mediated DNA uptake, and physical transfer by gene guns or electroporation can also be employed.

Another method for delivering CEs to selected tumor cells involves antibody-directed enzyme prodrug therapy (ADEPT). In this method, human tumors are targeted by conjugation of tumor-specific marker antibody with a molecule such as hCE1mut6. Cellular internalization of the complex and release of active CE is achieved, leading to CPT-11 activation that is specific for cells expressing the marker antigen. Since the array of marker molecules expressed upon the cell surface is different for each tumor type, markers specific for each targeted tumor type can be selected as appropriate. Similarly, the use of avidin-biotin-conjugated molecules to target tumor cells (Moro, et al. 1997. *Cancer Res.* 57:1922-1928) is also applicable for localization of the CE protein of the present invention to the cell surface followed by drug activation at the targeted cell.

Liver CE is localized in the endoplasmic reticulum. Removal of the six N-terminal amino acids results in secretion of active protein into the extracellular milieu. Both the secreted and the endoplasmic reticulum-localized protein can convert CPT-11 to SN-38; therefore, the potential exists for a bystander effect from cells expressing the secreted enzyme. A similar bystander effect has been demonstrated for other enzyme/prodrug combinations, such as HSVtk and ganciclovir (Dilber, et al. 1997. *Cancer Res.* 57:1523-1528), and results in increased cytotoxicity. Extracellular activation of CPT-11 may result in more efficient eradication of MRD in that uninfected neighboring tumor cells would be killed by exogenously produced SN-38. Gene therapy protocols with a secreted CE in combination with CPT-11 can therefore be more appropriate for the elimination of residual tumor tissue. Accordingly, it may be preferred to use a fragment of a polynucleotide encoding a polypeptide which is secreted, i.e., a polypeptide lacking the six N-terminal amino acid residues. An exemplary mutant human CE protein lacking the six N-terminal amino acid residues is set forth herein as SEQ ID NO:16. Additionally, recent reports indicate that the tethering of drug activating enzymes to the extracellular cell surface can result in anti-tumor activity in human tumor xenografts when combined with appropriate prodrug (Marais, et al. 1997. *Nature Biotech.* 15:1373-1377). A tethered enzyme generates a local bystander effect since the protein is not free to circulate in the plasma. Attachment of a CE of the present invention to the cell surface should result in local extracellular activation of CPT-11 to SN-38 and enhance local cell kill. Purging bone marrow of contaminating tumor cells will be accomplished by an intracellular enzyme, whereas eradication of MRD is better achieved by an enzyme that activates CPT-11 at an extracellular location.

Another aspect of the present invention that is contemplated is the application of the mutant human CE enzyme in the treatment of drug addiction. This use is contemplated based on work that has shown the ability of human CE to catalyze the hydrolysis of drugs such as heroin and cocaine (Redinbo, et al. 2003. *Biochemi. Soc. Trans.* 31:620-624; Bencharit, et al. 2003. *Nat. Struct. Biol.* 10:349-356). As such, the use of the instant mutant human CE enzyme to affect drug metabolism can be exploited as a method for treatment of drug addiction, as would be appreciated by one of skill in the art. In general, this application of the mutant human CE enzyme would be in a manner similar to the use of the enzyme in treatment of cancer.

In yet another aspect of the present invention that is contemplated based on the results described herein, the mutant human CE enzyme could be used in a method for metabolizing certain types of chemical weapons agents, specifically organophosphate compounds. It has been shown that organophosphates can be efficiently hydrolyzed by human CE after a single point mutation in its active site (Redinbo, et al. 2003. *Biochemi. Soc. Trans.* 31:620-624). In this regard, the enzyme of the present invention can be administered to a subject in need of treatment, e.g., a subject exposed to or suspected of being exposed to a chemical weapon agent, and used as a preventative treatment against the toxicity resulting from exposure to organophosphates.

The CE of the present invention cleaves the COOC bond present as an ester linkage in CPT-11 to generate SN-38. Since this enzyme can also catalyze the activation of other compounds that contain such a linkage, the present invention also provides assays for screening for compounds that contain this and related moieties. In one embodiment, the assay of the present invention is conducted in a cell system using, for example, yeast, baculovirus, or human tumor cell lines. In this embodiment, compounds activated by CE are identified and assessed for anticancer activity by growth inhibition or clonogenic cell survival assays using cells expressing or lacking a CE of the present invention. Alternatively, compounds can be screened in cell-free assays using a CE of the present invention isolated from host cells expressing this enzyme. In this embodiment, the ability of the enzyme to cleave a COOC ester linkage of a candidate compound is measured directly in a standard enzyme assay buffer system containing a CE of the present invention. Known concentrations of candidate compounds can be added to assay tubes containing a biological buffer such as HEPES at pH 7.4 and the enzyme and incubated at 37° C. for a selected amount of time. The reaction is then terminated by addition of methanol. The assay tubes are then centrifuged and the supernatant analyzed for the presence of cleaved compound fragment. Analysis of the supernatant can be performed by any number of well-known techniques including, but not limited to, spectrofluorometric analysis, high pressure liquid chromatography or mass spectrometry.

Compounds which can be screened in accordance with the instant assay include small organic compounds as well as derivatives or analogs of known compounds which contain the COOC ester linkage (e.g., CPT-11). Compounds identified in these screening assays as potential anticancer prodrugs may require chemical modification for optimize their antitumor activity.

The following non-limiting examples are provided to further illustrate the claimed invention.

EXAMPLE 1

Materials and Methods

Cell Lines, Plasmids and Adenoviral Vectors. Cell lines were grown in 10% fetal bovine serum and 2 mM glutamine in an atmosphere of 10% $CO_2$ at 37° C.

Plasmids containing the cDNAs encoding hCE1, hiCE and rCE are known in the art (Danks, et al. 1999. *Clin. Cancer Res.* 5:917-924; Potter, et al. 1998. *Cancer Res.* 52:2646-2651; Khanna, et al. 2000. *Cancer Res.* 60:4725-4728). The Genbank accession numbers for these sequences are M73499 (Munger, et al. 1991. *J. Biol. Chem.* 266:18832-18838), Y09616 (Schwer, et al. 1997. *Biochem. Biophys. Res. Comm.* 233:117-12) and AF036930 (Potter, et al. 1998. *Cancer Res.* 52:2646-2651), respectively. All of the plasmids, cell lines and adenoviral vectors used in these studies are listed in Table 7.

TABLE 7

| Name | Description | Details |
|---|---|---|
| PCIneo* | Mammalian expression vector | Obtained from Promega |
| pCIhCE1* | pCIneo containing wild-type hCE1 cDNA | From Danks, et al. 1999. *Clin. Cancer Res.* 5: 917-924 |
| pCIrCE* | pCIneo containing wild-type rCE cDNA | From Potter, et al. 1998. *Cancer Res.* 52: 2646-2651 |
| pCIhCE1m2* | pCIneo containing mutant hCE1 cDNA | M363L, L364M |
| pCIhCE1m3* | pCIneo containing mutant hCE1 cDNA | M363L, L364M, K459R |
| pCIhCE1m4* | pCIneo containing mutant hCE1 cDNA | M363L, L364M, K459R, F448Y, Q449R |
| pCIhCE1m5* | pCIneo containing mutant hCE1 cDNA | M363L, L364M, K459R, F448Y, Q449R, L357I, S365G |
| pCIhCE1m6* | pCIneo containing mutant hCE1 cDNA | M363L, L364M, K459R, F448Y, Q449R, L357I, S365G, Q361 insertion |
| pIRESneo* | Mammalian expression vector | Contains G418 resistance gene coupled to an IRES sequence |
| pIRESrCE* | pIRESneo containing rCE cDNA | From Potter, et al. 1998. *Cancer Res.* 52: 2646-2651 |
| pIREShCE1* | pIRESneo containing hCE1 cDNA | From Danks, et al. 1999. *Clin. Cancer Res.* 5: 917-924 |
| pIREShiCE* | pIRESneo containing hiCE cDNA | Expresses hiCE following transfection and selection with G418 |
| pIREShCE1m6* | pIRESneo containing hCE1m6 cDNA | Contains mutations as listed above for pCIhCE1m6 |
| COS-7[#] | African green monkey kidney cell line | Obtained from the America Type Culture Collection |
| U373MG[#] | Human astrocytoma cell line | Obtained from the America Type Culture Collection |
| U373IRES[#] | U373MG transfected with pIRESneo | G418 resistant but lacking exogenous CE expression |
| U373hCE1[#] | U373MG transfected with pIREShCE1 | U373MG expressing hCE1 |
| U373rCE[#] | U373MG transfected with pIRESrCE | U373MG expressing rCE |
| U373hiCE[#] | U373MG transfected with pIREShiCE | U373MG expressing hiCE |
| U373hCE1m6[#] | U373MG transfected with pIREShCE1m6 | U373MG expressing hCE1m6 |
| 293[#] | Human embryo kidney cell line | Obtained from the America Type Culture Collection |

TABLE 7-continued

| Name | Description | Details |
|---|---|---|
| Rh30[#] | Rhabdomyosarcoma cell line | From Douglass, et al. 1987. *Cytogenet. Cell Genet.* 45: 148-155 |
| SK-N-AS[#] | Neuroblastoma cell line | Obtained from the America Type Culture Collection |
| AdVC[†] | Adenovirus vector based upon Ad5 | E1, E3-deleted Ad vector |
| AdCMVrCE[†] | Adenovirus containing rCE cDNA | Expresses high levels of rCE under control of CMV promoter |
| AdCMVhCE1m6[†] | Adenovirus containing hCE1m6 cDNA | Expresses high levels of hCE1m6 under control of CMV promoter |

*plasmid;
[#]cell line;
[†]adenovirus.

Analysis of Carboxylesterase Crystal Structures. The x-ray crystal structures of rCE (PDB 1K4Y; Bencharit, et al. 2002. *Nat. Struct. Biol.* 9:337-342)) and hCE1 (PDB 1MX5; Bencharit, et al. 2003. *Chem. Biol.* 10:341-349; Bencharit, et al. 2003. *Nat. Struct. Biol.* 10:349-356) were overlaid and examined using ICM Pro software (Molsoft, San Diego Calif.).

Site-Directed Mutagenesis. Site-directed mutagenesis was achieved using a QuickChange site-directed mutagenesis kit (Stratagene, La Jolla, Calif.) with custom primers designed to produce the desired mutations. All mutants were subjected to DNA sequencing to confirm the identity of the clones.

Carboxylesterase Assays. CE activity was determined using a spectrophotometric assay with 3 mM o-nitrophenyl acetate (o-NPA) as a substrate (Potter, et al. 1998. *Cancer Res.* 52:2646-2651; Wierdl, et al. 2001. *Cancer Res.* 61:5078-5082; Beaufay, et al. 1974. *J. Cell Biol.* 61:188-200). Data were expressed as nmoles o-nitrophenol produced per minute per milligram of protein. To correct for differences in CE expression within transfected cells, the enzyme activity values were corrected for the level of immuno-reactive CE protein as determined from western analyses.

Transfection of Cell Lines. Transient transfection of Cos7 cells was achieved by electroporation (Potter, et al. 1998. *Cancer Res.* 52:2646-2651). For the generation of stable cell lines, cDNAs were ligated into pIRESneo and U373MG cells were electroporated under similar conditions. Transfectants were selected in media containing 400 μg/ml of G418. Since the CE cDNA was linked via an internal ribosome entry sequence (IRES) to the neomycin gene, selection of individual G418-resistant clones was not necessary. Routinely, whole cell sonicates obtained from these pooled populations of cells contained 200-500 nmoles/min/mg of CE activity.

CPT-11 Conversion Assays. Conversion of CPT-11 to SN-38 was monitored by incubating cell extracts with 5 μM CPT-11 for 1 hour in 50 mM Hepes pH7.4 at 37° C. An equal volume of acidified methanol was added to terminate the reactions and particulate matter was removed by centrifugation at 100,000 g for 5 minutes at 4° C. Concentrations of both drugs in the supernatant were then determined by HPLC (Guichard, et al. 1998. *Clin. Cancer Res.* 4:3089-3094; Morton, et al. 2000. *Cancer Res.* 60:4206-4210).

Protein Purification. Secreted forms of hCE1, rCE and mutant human CE were expressed in *Spodoptera frugiperda* Sf9 cells and purified from serum-free culture media according to known methods (Morton & Potter. 2000. *Mol. Biotechnol.* 16:193-202). For hiCE, an alternative purification procedure was developed using DEAE chromatography and elution with a pH/salt gradient.

Determination of Kinetic Parameters for Substrate Hydrolysis. $K_m$, $V_{max}$ and $k_{cat}$ values for the hydrolysis of CPT-11 by the recombinant purified proteins were determined using standard methods (Wadkins, et al. 2001. *Mol. Pharmacol.* 60:355-362).

Western Analysis. Cell extracts were separated in 4-20% pre-cast SDS-PAGE gels (Invitrogen, Carlsbad, Calif.) and following transfer to Immobilon-P membranes by electroblotting (Matsuidaira. 1990. *Methods Enzymol.* 182:602-613), western analysis was performed using known methods (Morton & Potter. 1998. *J. Pharmacol. Expt. Therap.* 286:1066-1073). CEs were identified using an anti-peptide antibody raised against the C-terminal amino acids CEKPPQTEHIEL (SEQ ID NO:15) of hCE1, and ECL detection (Amersham Life Sciences, Arlington Heights, Ill.). In all experiments, membranes were re-probed with an anti-TFIID antibody to confirm equal loading, and to correct for any differences in total protein. The molecular weight of immuno-reactive bands was determined using pre-stained molecular weight protein markers (Pierce, Rockford, Ill.). Densitometric quantitation of CE expression was performed using One-Dscan gel analysis software (Scanalytics Inc, Fairfax, Va.).

Construction of adenovirus. Replication-deficient adenovirus expressing hCE1m6 or rCE were constructed using standard protocols (Wierdl, et al. 2001. *Cancer Res.* 61:5078-5082). Multiplicity of infection (moi) was defined as the number of plaques produced in $1\times10^6$ 293 cells in a total volume of 1 ml of media after incubation with virus for 1 hour. Typically for $IC_{50}$ determinations an moi of 5 was used, however, using these conditions in U373MG cells resulted very high levels of transgene expression, leading to toxicity, Therefore an moi of 1 was used for this cell line.

Growth Inhibition Assays. Growth inhibition assays using CPT-11 were performed in triplicate in 6 well multiwell plates as previously described (Wierdl, et al. 2004. *Biochemistry* 43:1874-1882). The concentrations of drug required to inhibit cell growth by 50% ($IC_{50}$ values) were calculated using Prism software (GraphPad Software, San Diego, Calif.).

EXAMPLE 2

In Vitro Biological Activity of CE

The in vitro activity of rabbit liver CE can be examined in tumor cell lines. The growth inhibition of CPT-11 is compared in cells with and without hCE1mut6. The cells used can be Rh30 cells (107) that have been electroporated with a plasmid DNA or plasmid containing CE cDNA in a volume of phosphate-buffered saline. The cells are plated into 75-cm² flasks in fresh media and G418 added hours following transfection to select for cells expressing the neo gene and the CE. Cells are grown for a minimum of 10 days before use in growth inhibition experiments.

In one type of assay, CPT-11 is pre-incubated with hCE1mut6 to produce SN-38 prior to exposure of the cells to drug. For example, 0.5 to 5 units of hCE1mut6 are incubated with 1 M CPT-11 at 37° C. in DMEM medium for 2 hours. Each reaction mixture is filter-sterilized and Rh30 cells exposed to drug for one hour, at which time the medium is replaced with drug-free medium containing serum. Enzyme that has been inactivated by boiling for five minutes prior to incubation with drug or CPT-11 to which no enzyme has been added is used as negative controls. Cells are allowed to grow for three cell doubling times and cell numbers are determined.

In another type of growth inhibition assay, Rh30 cells transfected with either parent plasmid DNA or the plasmid containing the mutant human CE cDNA are exposed to different concentrations of CPT-11. Drug is added to tissue culture medium of each of the stably transfected cell lines for two hours, after which time the medium is replaced with drug-free medium. Cells are then allowed to grow for three cell doublings as before. Results are expressed as the concentration of drug required to reduce cell growth to 50% of control cells, or $IC_{50}$.

EXAMPLE 3

Use of CE in an In Vivo Model for Minimal Residual Disease (MRD)

A xenograft model for MRD has been developed to demonstrate the effectiveness of the combination of hCE1mut6 and prodrug in the prevention of MRD. In this model, immune-deprived mice, i.e., SCID mice, bearing human NB-1691 xenografts are treated with 10 mg/kg CPT-11 daily for 5 days on two consecutive weeks and tumor regression is examined. However, within 4-6 weeks, tumors are palpable in the exact position where the original xenograft was implanted. Since these tumors arise from cells that survived the initial cycle of chemotherapy, this model therefore mimics results seen in patients following surgical resection of the primary tumor and subsequent regrowth at the same site.

Experiments are performed in this model to compare the responses of mice bearing human Rh30 xenografts as well as xenografts expressing the hCE1mut6 protein. Rh30 rhabdosarcoma xenografts are transfected with a plasmid containing the cDNA for hCE1mut6 and with G418. Expression of CE is confirmed by biochemical assay using the CE substrate o-NPA and maintained for at least 12 weeks. Two groups of SCID mice are injected with the transfected cells subcutaneously into the flanks. A third group of control mice is injected in identical fashion with Rh30 cells not transfected with the plasmid. When the tumors reach a size of approximately 1 cm³, 2.5 mg CPT-11/kg/day is administered five days each week for two weeks (one cycle of therapy), repeated every 21 days for a total of three cycles (over 8 weeks) to one group of mice injected with the transfected xenograft cells and the third group of control mice. Tumor regression is examined.

Experiments can also be performed employing U373 glioblastoma cells transfected with a control plasmid or with a plasmid containing the cDNA for the hCE1mut6 protein. Expression of CE in the tumor cells is confirmed by biochemical assay using the substrate o-NPA. Cells are injected subcutaneously into the flanks of the SCID mice. When tumors reach approximately 1 cm³ in size, CPT-11 is administered daily for five days each week as described above, for three cycles, at a dose of 7.5 mg/kg/day. Again, tumor regression is examined.

EXAMPLE 4

Use of a Human CE/prodrug Combination to Purge Bone Marrow of Tumor Cells

Intravenous injection of human neuroblastoma NB-1691 tumor cells into immune-deprived mice results in the development of widespread metastatic disease with death occurring on days 36-38. Since both synaptophysin and tyrosine hydroxylase expression are specific for neuroblastoma cells, RT/PCR analysis of these mRNAs can detect tumor cells present in mixed populations of cells. Circulating neuroblastoma cells can be detected in the peripheral blood of these animals 36 days after injection with NB-1691. Studies then determine whether the bone marrow of these same animals contains neuroblastoma cells. The success of ex vivo purging of bone marrow with the hCE1mut6/CPT-11 combination is demonstrated by transplanting purged bone marrow into lethally irradiated mice. If mice remain disease free for extended periods of time, this indicates that the CE/prodrug purging therapy kills neuroblastoma cells in the donor marrow.

EXAMPLE 5

Treatment of Minimal Residual Disease (MRD) in Humans

The mutant human CE in combination with CPT-11 or other prodrug(s) activated by this enzyme are used to purge bone marrow of residual tumor cells prior to autologous bone marrow transplants to prevent recurrence of local MRD following removal of bulk tumor by surgery or chemotherapy. Following debulking of the primary tumor, adenovirus containing the mutant human CE under the control of a tumor-specific responsive promoter is applied to the tumor margins at either the time of surgery, by stereotaxic injection, or by implantation of a time-release polymer or other material. Anti-tumor effect of single application at time of surgery is compared with the effect produced by repetitive or time-release use of adenoviral constructs. Adenovirus dose ranges from $10^6$ to $10^{10}$ plaque-forming units as has been reported to be effective for intratumoral injection of adenovirus (Heise, et al. 1977. *Nature Med.* 3:639-645). CPT-11 is administered over the next one to six weeks to elicit tumor selective cell kill. Doses and schedules of CPT-11 are determined in clinical trials of CPT-11 by itself and in human xenograft model systems to produce maximal tumor effect.

EXAMPLE 6

Purging Bone Marrow of Tumor Cells in Humans

Tumor cells that contaminate bone marrow used for autologous transplant contribute to relapse of disease. Therefore, the mutant human CE can be used in combination with a suitable prodrug to eradicate tumor cells in marrow samples to be used for transplant. This approach maintains the viability of hematopoietic cells required for reconstitution. Bone marrow samples are transduced ex vivo with adenovirus containing the mutant human CE cDNA, using a multiplicity of infection (moi) that will infect 100% of the tumor cells.

Typically, a moi of 0.5 to 10 is adequate for tumor cells, while a moi of 100 to 1,000 is required to transduce a majority of hematopoietic progenitor cells. Two days following adenoviral transduction, cells are exposed for two hours to a range of CPT-11 concentrations, usually varying from 50 nM to 100 μM. Two days after exposure to drug, the marrow sample is harvested and stored for reinfusion into the patient and reconstitution of a tumor-free marrow.

What is claimed is:

1. An isolated polypeptide as set forth in SEQ ID NO:3.

2. A method of inhibiting tumor recurrence in a patient comprising:
   (a) surgically removing a tumor from a patient;
   (b) administering the polypeptide of claim 1 at the site of tumor resection; and
   (c) administering a chemotherapeutic prodrug systemically so that tumor recurrence is inhibited.

3. The method of claim 2, wherein the chemotherapeutic prodrug is CPT-11.

4. A method for treating drug addiction comprising administering to a subject in need of treatment an effective amount of the polypeptide of claim 1 thereby treating the subject's drug addiction.

5. A method for facilitating the metabolism of an organophosphate comprising administering to a subject having been exposed to an organophosphate an effective amount of the polypeptide of claim 1 thereby facilitating the metabolism of the organophosphate.

* * * * *

```
                        SEQUENCE LISTING

<160> NUMBER OF SEQ ID NOS: 16

<210> SEQ ID NO 1
<211> LENGTH: 566
<212> TYPE: PRT
<213> ORGANISM: Homo sapiens

<400> SEQUENCE: 1

Met Trp Leu Arg Ala Phe Ile Leu Ala Thr Leu Ser Ala Ser Ala Ala
1               5                   10                  15

Trp Gly His Pro Ser Ser Pro Val Val Asp Thr Val His Gly Lys
            20                  25                  30

Val Leu Gly Lys Phe Val Ser Leu Glu Gly Phe Ala Gln Pro Val Ala
            35                  40                  45

Ile Phe Leu Gly Ile Pro Phe Ala Lys Pro Pro Leu Gly Pro Leu Arg
    50                  55                  60

Phe Thr Pro Pro Gln Pro Ala Glu Pro Trp Ser Phe Val Lys Asn Ala
65                  70                  75                  80

Thr Ser Tyr Pro Pro Met Cys Thr Gln Asp Pro Lys Ala Gly Gln Leu
                85                  90                  95

Leu Ser Glu Leu Phe Thr Asn Arg Lys Glu Asn Ile Pro Leu Lys Leu
            100                 105                 110

Ser Glu Asp Cys Leu Tyr Leu Asn Ile Tyr Thr Pro Ala Asp Leu Thr
        115                 120                 125

Lys Lys Asn Arg Leu Pro Val Met Val Trp Ile His Gly Gly Gly Leu
    130                 135                 140

Met Val Gly Ala Ala Ser Thr Tyr Asp Gly Leu Ala Leu Ala Ala His
145                 150                 155                 160

Glu Asn Val Val Val Thr Ile Gln Tyr Arg Leu Gly Ile Trp Gly
                165                 170                 175

Phe Phe Ser Thr Gly Asp Glu His Ser Arg Gly Asn Trp Gly His Leu
            180                 185                 190

Asp Gln Val Ala Ala Leu Arg Trp Val Gln Asp Asn Ile Ala Ser Phe
        195                 200                 205

Gly Gly Asn Pro Gly Ser Val Thr Ile Phe Gly Glu Ser Ala Gly Gly
    210                 215                 220

Glu Ser Val Ser Val Leu Val Leu Ser Pro Leu Ala Lys Asn Leu Phe
225                 230                 235                 240

His Arg Ala Ile Ser Glu Ser Gly Val Ala Leu Thr Ser Val Leu Val
                245                 250                 255

Lys Lys Gly Asp Val Lys Pro Leu Ala Glu Gln Ile Ala Ile Thr Ala
            260                 265                 270

Gly Cys Lys Thr Thr Thr Ser Ala Val Met Val His Cys Leu Arg Gln
        275                 280                 285

Lys Thr Glu Glu Glu Leu Leu Glu Thr Thr Leu Lys Met Lys Phe Leu
    290                 295                 300

Ser Leu Asp Leu Gln Gly Asp Pro Arg Glu Ser Gln Pro Leu Leu Gly
305                 310                 315                 320

Thr Val Ile Asp Gly Met Leu Leu Leu Lys Thr Pro Glu Glu Leu Gln
                325                 330                 335
```

Ala Glu Arg Asn Phe His Thr Val Pro Tyr Met Val Gly Ile Asn Lys
            340                 345                 350

Gln Glu Phe Gly Trp Leu Ile Pro Met Leu Met Ser Tyr Pro Leu Ser
        355                 360                 365

Glu Gly Gln Leu Asp Gln Lys Thr Ala Met Ser Leu Leu Trp Lys Ser
370                 375                 380

Tyr Pro Leu Val Cys Ile Ala Lys Glu Leu Ile Pro Glu Ala Thr Glu
385                 390                 395                 400

Lys Tyr Leu Gly Gly Thr Asp Asp Thr Val Lys Lys Lys Asp Leu Phe
                405                 410                 415

Leu Asp Leu Ile Ala Asp Val Met Phe Gly Val Pro Ser Val Ile Val
                420                 425                 430

Ala Arg Asn His Arg Asp Ala Gly Ala Pro Thr Tyr Met Tyr Glu Phe
            435                 440                 445

Gln Tyr Arg Pro Ser Phe Ser Ser Asp Met Lys Pro Lys Thr Val Ile
        450                 455                 460

Gly Asp His Gly Asp Glu Leu Phe Ser Val Phe Gly Ala Pro Phe Leu
465                 470                 475                 480

Lys Glu Gly Ala Ser Glu Glu Ile Arg Leu Ser Lys Met Val Met
                485                 490                 495

Lys Phe Trp Ala Asn Phe Ala Arg Asn Gly Asn Pro Asn Gly Glu Gly
                500                 505                 510

Leu Pro His Trp Pro Glu Tyr Asn Gln Lys Glu Gly Tyr Leu Gln Ile
            515                 520                 525

Gly Ala Asn Thr Gln Ala Ala Gln Lys Leu Lys Asp Lys Glu Val Ala
        530                 535                 540

Phe Trp Thr Asn Leu Phe Ala Lys Lys Ala Val Glu Lys Pro Pro Gln
545                 550                 555                 560

Thr Glu His Ile Glu Leu
                565

<210> SEQ ID NO 2
<211> LENGTH: 505
<212> TYPE: PRT
<213> ORGANISM: Oryctolagus cuniculus

<400> SEQUENCE: 2

Gly Ser Leu Arg Phe Ala Pro Pro Gln Pro Ala Glu Ser Trp Ser His
1               5                   10                  15

Val Lys Asn Thr Thr Ser Tyr Pro Pro Met Cys Ser Gln Asp Ala Val
                20                  25                  30

Ser Gly His Met Leu Ser Glu Leu Phe Thr Asn Arg Lys Glu Asn Ile
            35                  40                  45

Pro Leu Lys Phe Ser Glu Asp Cys Leu Tyr Leu Asn Ile Tyr Thr Pro
        50                  55                  60

Ala Asp Leu Thr Lys Arg Gly Arg Leu Pro Val Met Val Trp Ile His
65                  70                  75                  80

Gly Gly Gly Leu Met Val Gly Gly Ala Ser Thr Tyr Asp Gly Leu Ala
                85                  90                  95

Leu Ser Ala His Glu Asn Val Val Val Thr Ile Gln Tyr Arg Leu
            100                 105                 110

Gly Ile Trp Gly Phe Phe Ser Thr Gly Asp Glu His Ser Arg Gly Asn
        115                 120                 125

Trp Gly His Leu Asp Gln Val Ala Ala Leu Arg Trp Val Gln Asp Asn
130                 135                 140

```
Ile Ala Asn Phe Gly Gly Asp Pro Gly Ser Val Thr Ile Phe Gly Glu
145                 150                 155                 160

Ser Ala Gly Gly Gln Ser Val Ser Ile Leu Leu Ser Pro Leu Thr
            165                 170                 175

Lys Asn Leu Phe His Arg Ala Ile Ser Glu Ser Gly Val Ala Leu Leu
                180                 185                 190

Ser Ser Leu Phe Arg Lys Asn Thr Lys Ser Leu Ala Glu Lys Ile Ala
            195                 200                 205

Ile Glu Ala Gly Cys Lys Thr Thr Thr Ser Ala Val Met Val His Cys
210                 215                 220

Leu Arg Gln Lys Thr Glu Glu Leu Met Glu Val Thr Leu Lys Met
225                 230                 235                 240

Lys Phe Met Ala Leu Asp Leu Val Gly Asp Pro Lys Glu Asn Thr Ala
                245                 250                 255

Phe Leu Thr Thr Val Ile Asp Gly Val Leu Leu Pro Lys Ala Pro Ala
            260                 265                 270

Glu Ile Leu Ala Glu Lys Lys Tyr Asn Met Leu Pro Tyr Met Val Gly
            275                 280                 285

Ile Asn Gln Gln Glu Phe Gly Trp Ile Ile Pro Met Gln Met Leu Gly
290                 295                 300

Tyr Pro Leu Ser Glu Gly Lys Leu Asp Gln Lys Thr Ala Thr Glu Leu
305                 310                 315                 320

Leu Trp Lys Ser Tyr Pro Ile Val Asn Val Ser Lys Glu Leu Thr Pro
                325                 330                 335

Val Ala Thr Glu Lys Tyr Leu Gly Gly Thr Asp Asp Pro Val Lys Lys
            340                 345                 350

Lys Asp Leu Phe Leu Asp Met Leu Ala Asp Leu Leu Phe Gly Val Pro
            355                 360                 365

Ser Val Asn Val Ala Arg His His Arg Asp Ala Gly Ala Pro Thr Tyr
370                 375                 380

Met Tyr Glu Tyr Arg Tyr Arg Pro Ser Phe Ser Ser Asp Met Arg Pro
385                 390                 395                 400

Lys Thr Val Ile Gly Asp His Gly Asp Glu Ile Phe Ser Val Leu Gly
                405                 410                 415

Ala Pro Phe Leu Lys Glu Gly Ala Thr Glu Glu Glu Ile Lys Leu Ser
            420                 425                 430

Lys Met Val Met Lys Tyr Trp Ala Asn Phe Ala Arg Asn Gly Asn Pro
            435                 440                 445

Asn Gly Glu Gly Leu Pro Gln Trp Pro Ala Tyr Asp Tyr Lys Glu Gly
450                 455                 460

Tyr Leu Gln Ile Gly Ala Thr Thr Gln Ala Ala Gln Lys Leu Lys Asp
465                 470                 475                 480

Lys Glu Val Ala Phe Trp Thr Glu Leu Trp Ala Lys Glu Ala Ala Arg
                485                 490                 495

Pro Arg Glu Thr Glu His Ile Glu Leu
                500                 505

<210> SEQ ID NO 3
<211> LENGTH: 567
<212> TYPE: PRT
<213> ORGANISM: Artificial Sequence
<220> FEATURE:
<223> OTHER INFORMATION: Synthetic mutant human carboxylesterase

<400> SEQUENCE: 3
```

```
Met Trp Leu Arg Ala Phe Ile Leu Ala Thr Leu Ser Ala Ser Ala Ala
1               5                   10                  15

Trp Gly His Pro Ser Ser Pro Val Val Asp Thr Val His Gly Lys
            20                  25                  30

Val Leu Gly Lys Phe Val Ser Leu Glu Gly Phe Ala Gln Pro Val Ala
            35                  40                  45

Ile Phe Leu Gly Ile Pro Phe Ala Lys Pro Pro Leu Gly Pro Leu Arg
        50                  55                  60

Phe Thr Pro Pro Gln Pro Ala Glu Pro Trp Ser Phe Val Lys Asn Ala
65                      70                  75                  80

Thr Ser Tyr Pro Pro Met Cys Thr Gln Asp Pro Lys Ala Gly Gln Leu
                85                  90                  95

Leu Ser Glu Leu Phe Thr Asn Arg Lys Glu Asn Ile Pro Leu Lys Leu
            100                 105                 110

Ser Glu Asp Cys Leu Tyr Leu Asn Ile Tyr Thr Pro Ala Asp Leu Thr
            115                 120                 125

Lys Lys Asn Arg Leu Pro Val Met Val Trp Ile His Gly Gly Gly Leu
        130                 135                 140

Met Val Gly Ala Ala Ser Thr Tyr Asp Gly Leu Ala Leu Ala Ala His
145                 150                 155                 160

Glu Asn Val Val Val Thr Ile Gln Tyr Arg Leu Gly Ile Trp Gly
                165                 170                 175

Phe Phe Ser Thr Gly Asp Glu His Ser Arg Gly Asn Trp Gly His Leu
            180                 185                 190

Asp Gln Val Ala Ala Leu Arg Trp Val Gln Asp Asn Ile Ala Ser Phe
        195                 200                 205

Gly Gly Asn Pro Gly Ser Val Thr Ile Phe Gly Glu Ser Ala Gly Gly
        210                 215                 220

Glu Ser Val Ser Val Leu Val Leu Ser Pro Leu Ala Lys Asn Leu Phe
225                 230                 235                 240

His Arg Ala Ile Ser Glu Ser Gly Val Ala Leu Thr Ser Val Leu Val
                245                 250                 255

Lys Lys Gly Asp Val Lys Pro Leu Ala Glu Gln Ile Ala Ile Thr Ala
            260                 265                 270

Gly Cys Lys Thr Thr Thr Ser Ala Val Met Val His Cys Leu Arg Gln
        275                 280                 285

Lys Thr Glu Glu Glu Leu Leu Glu Thr Thr Leu Lys Met Lys Phe Leu
            290                 295                 300

Ser Leu Asp Leu Gln Gly Asp Pro Arg Glu Ser Gln Pro Leu Leu Gly
305                 310                 315                 320

Thr Val Ile Asp Gly Met Leu Leu Lys Thr Pro Glu Glu Leu Gln
                325                 330                 335

Ala Glu Arg Asn Phe His Thr Val Pro Tyr Met Val Gly Ile Asn Lys
            340                 345                 350

Gln Glu Phe Gly Trp Ile Ile Pro Met Gln Met Leu Gly Tyr Pro Leu
        355                 360                 365

Ser Glu Gly Gln Leu Asp Gln Lys Thr Ala Met Ser Leu Leu Trp Lys
        370                 375                 380

Ser Tyr Pro Leu Val Cys Ile Ala Lys Glu Leu Ile Pro Glu Ala Thr
385                 390                 395                 400

Glu Lys Tyr Leu Gly Gly Thr Asp Asp Thr Val Lys Lys Asp Leu
                405                 410                 415

Phe Leu Asp Leu Ile Ala Asp Val Met Phe Gly Val Pro Ser Val Ile
            420                 425                 430
```

Val Ala Arg Asn His Arg Asp Ala Gly Ala Pro Thr Tyr Met Tyr Glu
        435                 440                 445

Tyr Arg Tyr Arg Pro Ser Phe Ser Ser Asp Met Arg Pro Lys Thr Val
450                 455                 460

Ile Gly Asp His Gly Asp Glu Leu Phe Ser Val Phe Gly Ala Pro Phe
465                 470                 475                 480

Leu Lys Glu Gly Ala Ser Glu Glu Ile Arg Leu Ser Lys Met Val
            485                 490                 495

Met Lys Phe Trp Ala Asn Phe Ala Arg Asn Gly Asn Pro Asn Gly Glu
            500                 505                 510

Gly Leu Pro His Trp Pro Glu Tyr Asn Gln Lys Glu Gly Tyr Leu Gln
            515                 520                 525

Ile Gly Ala Asn Thr Gln Ala Ala Gln Lys Leu Lys Asp Lys Glu Val
            530                 535                 540

Ala Phe Trp Thr Asn Leu Phe Ala Lys Lys Ala Val Glu Lys Pro Pro
545                 550                 555                 560

Gln Thr Glu His Ile Glu Leu
            565

<210> SEQ ID NO 4
<211> LENGTH: 1763
<212> TYPE: DNA
<213> ORGANISM: Homo sapiens

<400> SEQUENCE: 4
atctaaagcg agaactgtcg cccttcacga tgtggctccg tgcctttatc ctggccactc      60
tctctgcttc cgcggcttgg gggcatccgt cctcgccacc tgtggtggac accgtgcatg     120
gcaaagtgct ggggaagttc gtcagcttag aaggatttgc acagcctgtg ccattttcc      180 tgggaatccc ttttgccaag ccgcctcttg accccctgag gtttactcca ccgcagcctg     240
cagaaccatg gagctttgtg aagaatgcca cctcgtaccc tcctatgtgc acccaagatc     300
ccaaggcggg gcagttactc tcagagctat ttacaaaccg aaaggagaac attcctctca     360
agctttctga agactgtctt tacctcaata tttacactcc tgctgacttg accaagaaaa     420
acaggctgcc ggtgatggtg tggatccacg agggggggct gatggtgggt gcggcatcaa     480
cctatgatgg gctggccctt gctgccatg aaaacgtggt ggtggtgacc attcaatatc     540
gcctgggcat ctggggattc ttcagcacag gggatgaaca cagccggggg aactggggtc     600
acctggacca ggtggctgcc ctgcgctggg tccaggacaa cattgccagc tttgagggga     660
acccaggctc tgtgaccatc tttggagagt cagcgggagg agaaagtgtc tctgttcttg     720
ttttgtctcc attggccaag aacctcttcc accgggccat ttctgagagt ggcgtggccc     780
tcacttctgt tctggtgaag aaaggtgatg tcaagccctt ggctgagcaa attgctatca     840
ctgctgggtg caaaccacc acctctgctg tcatggttca ctgcctgcga cagaagacgg     900
aagaggagct cttggagacg acattgaaaa tgaaattctt atctctggac ttacagggag     960
accccagaga gagtcaaccc cttctgggca ctgtgattga tgggatgctg ctgctgaaaa    1020
cacctgaaga gcttcaagct gaaaggaatt ccacactgt ccctacatg gtcggaatta    1080 acaagcagga gtttggctgg ttgattccaa tgttgatgag ctatccactc tccgaagggc    1140
aactggacca gaagacagcc atgtcactcc tgtggaagtc ctatccctt gtttgcattg    1200 ctaaggaact gattccagaa gccactgaga atacttagg aggaacagac gacactgtca    1260 aaagaaaga cctgttcctg gacttgatag cagatgtgat gtttggtgtc ccatctgtga    1320

| | |
|---|---|
| ttgtggcccg gaaccacaga gatgctggag cacccaccta catgtatgag tttcagtacc | 1380 |
| gtccaagctt ctcatcagac atgaaaccca agacggtgat aggagaccac ggggatgagc | 1440 |
| tcttctccgt ctttggggcc ccatttttaa aagagggtgc ctcagaagag gagatcagac | 1500 |
| ttagcaagat ggtgatgaaa ttctgggcca actttgctcg caatggaaac cccaatgggg | 1560 |
| aagggctgcc ccactggcca gagtacaacc agaaggaagg gtatctgcag attggtgcca | 1620 |
| acacccaggc ggcccagaag ctgaaggaca agaagtagc tttctggacc aacctctttg | 1680 |
| ccaagaaggc agtggagaag ccaccccaga cagaacacat agagctgtga atgaagatcc | 1740 |
| agccggcctt gggagcctgg agg | 1763 |

<210> SEQ ID NO 5
<211> LENGTH: 1717
<212> TYPE: DNA
<213> ORGANISM: Oryctolagus cuniculus

<400> SEQUENCE: 5

| | |
|---|---|
| gaattctgcc atgtggctct gtgcattggc cctggcctct ctcgccgctt gcacggcttg | 60 |
| ggggcacccg tctgcaccac ctgtggtaga tactgtgcat ggcaaagtcc tggggaagtt | 120 |
| cgtcagctta aaggatttg cacagcccgt ggccgtcttc ctgggagtcc ccttcgccaa | 180 |
| gcccctctt ggatccctga ggtttgcacc accacagcct gcagaatcat ggagccacgt | 240 |
| gaagaacacc acctcctacc ctcccatgtg ctcccaggac gcagtatcag gcatatgct | 300 |
| ctcggagctc ttcaccaaca gaaaagagaa catccctctt aagttttctg aagactgcct | 360 |
| ttacctgaat atttacaccc ctgctgacct gacaaagaga ggcaggctgc cggtgatggt | 420 |
| gtggatccat ggaggtggtc tgatggtggg tggagcatca acctatgatg gcctggctct | 480 |
| ttctgcccat gagaacgtgg tggtggtgac cattcagtac cgcctgggca tctggggatt | 540 |
| cttcagcaca ggagatgagc acagccgagg gaactggggt cacttggacc aggtggctgc | 600 |
| gctgcggtgg gtccaggaca acattgccaa cttttggaggg gacccaggct ctgtgaccat | 660 |
| cttttggagag tcagcaggag gtcaaagtgt ctctatcctt ctattatccc ccctgaccaa | 720 |
| gaatctcttc catcgagcaa tttccgagag tggcgtggcc ctccttttcca gtctcttcag | 780 |
| gaagaacacc aagtccttgg ctgagaaaat tgccatcgaa gctgggtgta aaaccaccac | 840 |
| ctcggctgtc atggttcact gcctgcgcca aagacagag gaagaactca tggaggtgac | 900 |
| attgaaaatg aaatttatgg ctctagatct agttggcgac cccaaagaga acaccgcctt | 960 |
| cctgaccact gtgattgatg gggtgctgct gccaaaagca cctgcagaga ttctggcaga | 1020 |
| gaagaaatac aacatgctgc cctacatggt gggaatcaac cagcaagagt ttggctggat | 1080 |
| tatcccaatg caaatgctgg gctatccact ctctgaaggc aaactggacc agaagacagc | 1140 |
| tacagaactc ttgtggaagt cctaccccat tgtcaatgtc tctaaggagc tgactccagt | 1200 |
| ggccactgag aagtatttag gagggacaga tgaccctgtc aaaagaaag acttgttcct | 1260 |
| ggacatgctt gcagatttgt tatttggtgt cccatctgtg aatgtggctc gtcaccacag | 1320 |
| agatgctgga gcccccacct atatgtatga gtatcggtat cgcccaagct tctcatcaga | 1380 |
| catgagaccc aagacagtga taggggacca tggagatgag atcttctctg tcttaggagc | 1440 |
| cccgttttta aaagagggtg ccacagaaga ggagatcaaa ctgagcaaga tggtgatgaa | 1500 |
| atactgggcc aactttgcta ggaatgggaa tcccaatgga aagggcttc ctcaatggcc | 1560 |
| agcatatgac tacaaggaag gttacctgca gattggagcc accacccagg cagcccagaa | 1620 |
| actgaaagac aaggaagtgg cttttctgga ctgagctctgg gccaaggagg cagcaaggcc | 1680 | acgtgagaca gagcacattg agctgtgaat tgaattc 1717

<210> SEQ ID NO 6
<211> LENGTH: 16
<212> TYPE: PRT
<213> ORGANISM: Oryctolagus cuniculus

<400> SEQUENCE: 6

Gly Trp Ile Ile Pro Met Gln Met Leu Gly Tyr Pro Leu Ser Glu Gly
1               5                   10                  15

<210> SEQ ID NO 7
<211> LENGTH: 15
<212> TYPE: PRT
<213> ORGANISM: Homo sapiens

<400> SEQUENCE: 7

Gly Trp Leu Ile Pro Met Leu Met Ser Tyr Pro Leu Ser Glu Gly
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide

<400> SEQUENCE: 8

Gly Trp Leu Ile Pro Met Met Leu Ser Tyr Pro Leu Ser Glu Gly
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide

<400> SEQUENCE: 9

Gly Trp Ile Ile Pro Met Met Leu Gly Tyr Pro Leu Ser Glu Gly
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic peptide

<400> SEQUENCE: 10

Gly Trp Ile Ile Pro Met Gln Met Leu Gly Tyr Pro Leu Ser Glu Gly
1               5                   10                  15

<210> SEQ ID NO 11
<211> LENGTH: 18
<212> TYPE: PRT
<213> ORGANISM: Oryctolagus cuniculus

<400> SEQUENCE: 11

Tyr Arg Tyr Arg Pro Ser Phe Ser Ser Asp Met Arg Pro Lys Thr Val
1               5                   10                  15

Ile Gly

<210> SEQ ID NO 12
<211> LENGTH: 18
<212> TYPE: PRT

<213> ORGANISM: Homo sapiens

<400> SEQUENCE: 12

Phe Gln Tyr Arg Pro Ser Phe Ser Ser Asp Met Lys Pro Lys Thr Val
1               5                   10                  15

Ile Gly

<210> SEQ ID NO 13
<211> LENGTH: 18
<212> TYPE: PRT
<213> ORGANISM: Artificial Sequence
<220> FEATURE:
<223> OTHER INFORMATION: Synthetic peptide

<400> SEQUENCE: 13

Phe Gln Tyr Arg Pro Ser Phe Ser Ser Asp Met Arg Pro Lys Thr Val
1               5                   10                  15

Ile Gly

<210> SEQ ID NO 14
<211> LENGTH: 18
<212> TYPE: PRT
<213> ORGANISM: Artificial Sequence
<220> FEATURE:
<223> OTHER INFORMATION: Synthetic peptide

<400> SEQUENCE: 14

Tyr Arg Tyr Arg Pro Ser Phe Ser Ser Asp Met Arg Pro Lys Thr Val
1               5                   10                  15

Ile Gly

<210> SEQ ID NO 15
<211> LENGTH: 12
<212> TYPE: PRT
<213> ORGANISM: Artificial Sequence
<220> FEATURE:
<223> OTHER INFORMATION: Synthetic peptide

<400> SEQUENCE: 15

Cys Glu Lys Pro Pro Gln Thr Glu His Ile Glu Leu
1               5                   10

<210> SEQ ID NO 16
<211> LENGTH: 561
<212> TYPE: PRT
<213> ORGANISM: Artificial Sequence
<220> FEATURE:
<223> OTHER INFORMATION: Synthethic mutant human carboxylesterase

<400> SEQUENCE: 16

Ile Leu Ala Thr Leu Ser Ala Ser Ala Ala Trp Gly His Pro Ser Ser
1               5                   10                  15

Pro Pro Val Val Asp Thr Val His Gly Lys Val Leu Gly Lys Phe Val
                20                  25                  30

Ser Leu Glu Gly Phe Ala Gln Pro Val Ala Ile Phe Leu Gly Ile Pro
            35                  40                  45

Phe Ala Lys Pro Pro Leu Gly Pro Leu Arg Phe Thr Pro Pro Gln Pro
        50                  55                  60

Ala Glu Pro Trp Ser Phe Val Lys Asn Ala Thr Ser Tyr Pro Pro Met
65                  70                  75                  80

Cys Thr Gln Asp Pro Lys Ala Gly Gln Leu Leu Ser Glu Leu Phe Thr
                85                  90                  95

```
Asn Arg Lys Glu Asn Ile Pro Leu Lys Leu Ser Glu Asp Cys Leu Tyr
            100                 105                 110

Leu Asn Ile Tyr Thr Pro Ala Asp Leu Thr Lys Lys Asn Arg Leu Pro
            115                 120                 125

Val Met Val Trp Ile His Gly Gly Gly Leu Met Val Gly Ala Ala Ser
130                 135                 140

Thr Tyr Asp Gly Leu Ala Leu Ala Ala His Glu Asn Val Val Val Val
145                 150                 155                 160

Thr Ile Gln Tyr Arg Leu Gly Ile Trp Gly Phe Phe Ser Thr Gly Asp
                165                 170                 175

Glu His Ser Arg Gly Asn Trp Gly His Leu Asp Gln Val Ala Ala Leu
                180                 185                 190

Arg Trp Val Gln Asp Asn Ile Ala Ser Phe Gly Gly Asn Pro Gly Ser
                195                 200                 205

Val Thr Ile Phe Gly Glu Ser Ala Gly Gly Glu Ser Val Ser Val Leu
                210                 215                 220

Val Leu Ser Pro Leu Ala Lys Asn Leu Phe His Arg Ala Ile Ser Glu
225                 230                 235                 240

Ser Gly Val Ala Leu Thr Ser Val Leu Val Lys Lys Gly Asp Val Lys
                245                 250                 255

Pro Leu Ala Glu Gln Ile Ala Ile Thr Ala Gly Cys Lys Thr Thr Thr
                260                 265                 270

Ser Ala Val Met Val His Cys Leu Arg Gln Lys Thr Glu Glu Glu Leu
                275                 280                 285

Leu Glu Thr Thr Leu Lys Met Lys Phe Leu Ser Leu Asp Leu Gln Gly
                290                 295                 300

Asp Pro Arg Glu Ser Gln Pro Leu Leu Gly Thr Val Ile Asp Gly Met
305                 310                 315                 320

Leu Leu Leu Lys Thr Pro Glu Glu Leu Gln Ala Glu Arg Asn Phe His
                325                 330                 335

Thr Val Pro Tyr Met Val Gly Ile Asn Lys Gln Glu Phe Gly Trp Ile
                340                 345                 350

Ile Pro Met Gln Met Leu Gly Tyr Pro Leu Ser Glu Gly Gln Leu Asp
                355                 360                 365

Gln Lys Thr Ala Met Ser Leu Leu Trp Lys Ser Tyr Pro Leu Val Cys
                370                 375                 380

Ile Ala Lys Glu Leu Ile Pro Glu Ala Thr Glu Lys Tyr Leu Gly Gly
385                 390                 395                 400

Thr Asp Asp Thr Val Lys Lys Asp Leu Phe Leu Asp Leu Ile Ala
                405                 410                 415

Asp Val Met Phe Gly Val Pro Ser Val Ile Val Ala Arg Asn His Arg
                420                 425                 430

Asp Ala Gly Ala Pro Thr Tyr Met Tyr Glu Tyr Arg Tyr Arg Pro Ser
                435                 440                 445

Phe Ser Ser Asp Met Arg Pro Lys Thr Val Ile Gly Asp His Gly Asp
                450                 455                 460

Glu Leu Phe Ser Val Phe Gly Ala Pro Phe Leu Lys Glu Gly Ala Ser
465                 470                 475                 480

Glu Glu Glu Ile Arg Leu Ser Lys Met Val Met Lys Phe Trp Ala Asn
                485                 490                 495

Phe Ala Arg Asn Gly Asn Pro Asn Gly Glu Gly Leu Pro His Trp Pro
                500                 505                 510

Glu Tyr Asn Gln Lys Glu Gly Tyr Leu Gln Ile Gly Ala Asn Thr Gln
                515                 520                 525
```

```
Ala Ala Gln Lys Leu Lys Asp Lys Glu Val Ala Phe Trp Thr Asn Leu
    530                 535                 540

Phe Ala Lys Lys Ala Val Glu Lys Pro Pro Gln Thr Glu His Ile Glu
545                 550                 555                 560

Leu
```